(12) United States Patent
Cha et al.

(10) Patent No.: US 8,765,682 B2
(45) Date of Patent: Jul. 1, 2014

(54) METHOD FOR IN VIVO RESIDUE-SPECIFIC DOPA INCORPORATION INTO MUSSEL ADHESIVE PROTEINS

(71) Applicant: Postech Academy-Industry Foundation, Pohang-si (KR)

(72) Inventors: Hyung Joon Cha, Pohang-si (KR); Byeongseon Yang, Chuncheon-si (KR); Yoo Seong Choi, Daejeon (KR); Hyungdon Yun, Daegu (KR)

(73) Assignee: Postech Academy-Industry Foundation, Pohang-Si (KR)

( * ) Notice: Subject to any disclaimer, the term of this patent is extended or adjusted under 35 U.S.C. 154(b) by 0 days.

(21) Appl. No.: 13/917,766

(22) Filed: Jun. 14, 2013

(65) Prior Publication Data
US 2014/0005356 A1  Jan. 2, 2014

(30) Foreign Application Priority Data
Jun. 28, 2012 (KR) .................. 10-2012-0070246

(51) Int. Cl.
| A61K 38/16 | (2006.01) |
| C07H 21/04 | (2006.01) |
| C09J 189/00 | (2006.01) |
| C12N 5/10 | (2006.01) |
| C12P 21/06 | (2006.01) |
| A61P 17/02 | (2006.01) |
| C07K 14/435 | (2006.01) |
| C12N 15/63 | (2006.01) |

(52) U.S. Cl.
CPC ..................... *A61K 38/16* (2013.01)
USPC ...... 514/19.1; 530/350; 536/23.1; 435/320.1; 435/325; 435/419; 435/348; 435/69.1

(58) Field of Classification Search
None
See application file for complete search history.

(56) References Cited

PUBLICATIONS

Choi et al ("Recombinant mussel adhesive protein fp-5 (MAP fp-5) as a bulk bioadhesive and surface coating material." (Aug. 2011) Biofouling 27(7): 729-737).*
Byeongseon Yang, et al., "In Vivo DOPA Incorpor bon for Mussel Adhesive Protein", 2012 International Symposium & Annual Meeting, Susan, Korea, (Jun. 27, 2012).
Yoo Seong Choi, et al, "Recombinant mussel adhesive protein fp-5 (MAP fp-5) as a bulk bioadhesive and surface coating material", Biofouling. vol. 27, No. 7. pp. 729-737, (Aug. 2011).
Dong Soo Hwang, et al., "Practical recombinant hybrid mussel bioadhesive fp-151", Biomaterials, vol. 28, No. 24, pp. 3560-3568 (Aug. 2007).

* cited by examiner

*Primary Examiner* — Karlheinz R Skowronek
*Assistant Examiner* — Mindy Newman
(74) *Attorney, Agent, or Firm* — lexyoume ip meister

(57) ABSTRACT

The present invention relates to recombinant mussel adhesive protein wherein a DOPA residue is in vivo incorporated instead of a tyrosine residue, and a method for producing the same. More specifically, the present invention relates to recombinant mussel adhesive protein wherein a DOPA residue is incorporated instead of a tyrosine residue, and a method for producing the same, and a transformant for producing the recombinant mussel adhesive protein.

17 Claims, 8 Drawing Sheets

SEQUENCE LISTING

<160> NUMBER OF SEQ ID NOS: 33

<210> SEQ ID NO 1
<211> LENGTH: 196
<212> TYPE: PRT
<213> ORGANISM: Artificial Sequence
<220> FEATURE:
<223> OTHER INFORMATION: FP-151

<400> SEQUENCE: 1

Met Ala Lys Pro Ser Tyr Pro Pro Thr Tyr Lys Ala Lys Pro Ser Tyr
 1               5                  10                  15

Pro Pro Thr Tyr Lys Ala Lys Pro Ser Tyr Pro Pro Thr Tyr Lys Ala
                20                  25                  30

Lys Pro Ser Tyr Pro Pro Thr Tyr Lys Ala Lys Pro Ser Tyr Pro Pro
            35                  40                  45

Thr Tyr Lys Ala Lys Pro Ser Tyr Pro Pro Thr Tyr Lys Ser Ser Glu

```
                50                  55                  60
Glu Tyr Lys Gly Gly Tyr Tyr Pro Gly Asn Thr Tyr His Tyr His Ser
 65                  70                  75                  80

Gly Gly Ser Tyr His Gly Ser Gly Tyr His Gly Gly Tyr Lys Gly Lys
                 85                  90                  95

Tyr Tyr Gly Lys Ala Lys Lys Tyr Tyr Lys Tyr Lys Asn Ser Gly
            100                 105                 110

Lys Tyr Lys Tyr Leu Lys Lys Ala Arg Lys Tyr His Arg Lys Gly Tyr
            115                 120                 125

Lys Lys Tyr Tyr Gly Gly Ser Ser Ala Lys Pro Ser Tyr Pro Pro Thr
            130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
                165                 170                 175

Ala Lys Pro Ser Tyr Pro Pro Thr Tyr Lys Ala Lys Pro Ser Tyr Pro
                180                 185                 190

Pro Thr Tyr Lys
            195

<210> SEQ ID NO 2
<211> LENGTH: 202
<212> TYPE: PRT
<213> ORGANISM: Artificial Sequence
<220> FEATURE:
<223> OTHER INFORMATION: FP-151-RGD

<400> SEQUENCE: 2

Met Ala Lys Pro Ser Tyr Pro Pro Thr Tyr Lys Ala Lys Pro Ser Tyr
  1               5                  10                  15

Pro Pro Thr Tyr Lys Ala Lys Pro Ser Tyr Pro Pro Thr Tyr Lys Ala
                 20                  25                  30

Lys Pro Ser Tyr Pro Pro Thr Tyr Lys Ala Lys Pro Ser Tyr Pro Pro
             35                  40                  45

Thr Tyr Lys Ala Lys Pro Ser Tyr Pro Pro Thr Tyr Lys Ser Ser Glu
         50                  55                  60

Glu Tyr Lys Gly Gly Tyr Tyr Pro Gly Asn Thr Tyr His Tyr His Ser
 65                  70                  75                  80

Gly Gly Ser Tyr His Gly Ser Gly Tyr His Gly Gly Tyr Lys Gly Lys
                 85                  90                  95

Tyr Tyr Gly Lys Ala Lys Lys Tyr Tyr Lys Tyr Lys Asn Ser Gly
            100                 105                 110

Lys Tyr Lys Tyr Leu Lys Lys Ala Arg Lys Tyr His Arg Lys Gly Tyr
            115                 120                 125

Lys Lys Tyr Tyr Gly Gly Ser Ser Ala Lys Pro Ser Tyr Pro Pro Thr
            130                 135                 140

Tyr Lys Ala Lys Pro Ser Tyr Pro Pro Thr Tyr Lys Ala Lys Pro Ser
145                 150                 155                 160

Tyr Pro Pro Thr Tyr Lys Ala Lys Pro Ser Tyr Pro Pro Thr Tyr Lys
                165                 170                 175

Ala Lys Pro Ser Tyr Pro Pro Thr Tyr Lys Ala Lys Pro Ser Tyr Pro
                180                 185                 190

Pro Thr Tyr Lys Gly Arg Gly Asp Ser Pro
            195                 200
```

```
<210> SEQ ID NO 3
<211> LENGTH: 172
<212> TYPE: PRT
<213> ORGANISM: Artificial Sequence
<220> FEATURE:
<223> OTHER INFORMATION: FP-131

<400> SEQUENCE: 3

Met Ala Lys Pro Ser Tyr Pro Pro Thr Tyr Lys Ala Lys Pro Ser Tyr
 1               5                  10                  15

Pro Pro Thr Tyr Lys Ala Lys Pro Ser Tyr Pro Pro Thr Tyr Lys Ala
             20                  25                  30

Lys Pro Ser Tyr Pro Pro Thr Tyr Lys Ala Lys Pro Ser Tyr Pro Pro
         35                  40                  45

Thr Tyr Lys Ala Lys Pro Ser Tyr Pro Pro Thr Tyr Lys Pro Trp Ala
     50                  55                  60

Asp Tyr Tyr Gly Pro Lys Tyr Gly Pro Pro Arg Arg Tyr Gly Gly Gly
 65                  70                  75                  80

Asn Tyr Asn Arg Tyr Gly Arg Arg Tyr Gly Gly Tyr Lys Gly Trp Asn
                 85                  90                  95

Asn Gly Trp Lys Arg Gly Arg Trp Gly Arg Lys Tyr Tyr Gly Ser Ala
            100                 105                 110

Lys Pro Ser Tyr Pro Pro Thr Tyr Lys Ala Lys Pro Ser Tyr Pro Pro
        115                 120                 125

Thr Tyr Lys Ala Lys Pro Ser Tyr Pro Pro Thr Tyr Lys Ala Lys Pro
    130                 135                 140

Ser Tyr Pro Pro Thr Tyr Lys Ala Lys Pro Ser Tyr Pro Pro Thr Tyr
145                 150                 155                 160

Lys Ala Lys Pro Ser Tyr Pro Pro Thr Tyr Lys Leu
                165                 170

<210> SEQ ID NO 4
<211> LENGTH: 46
<212> TYPE: PRT
<213> ORGANISM: Artificial Sequence
<220> FEATURE:
<223> OTHER INFORMATION: FP-3

<400> SEQUENCE: 4

Ala Asp Tyr Tyr Gly Pro Lys Tyr Gly Pro Pro Arg Arg Tyr Gly Gly
 1               5                  10                  15

Gly Asn Tyr Asn Arg Tyr Gly Arg Arg Tyr Gly Gly Tyr Lys Gly Trp
             20                  25                  30

Asn Asn Gly Trp Lys Arg Gly Arg Trp Gly Arg Lys Tyr Tyr
         35                  40                  45

<210> SEQ ID NO 5
<211> LENGTH: 76
<212> TYPE: PRT
<213> ORGANISM: Artificial Sequence
<220> FEATURE:
<223> OTHER INFORMATION: FP-5

<400> SEQUENCE: 5

Ser Ser Glu Glu Tyr Lys Gly Gly Tyr Tyr Pro Gly Asn Thr Tyr His
 1               5                  10                  15

Tyr His Ser Gly Gly Ser Tyr His Gly Ser Gly Tyr His Gly Gly Tyr
             20                  25                  30

Lys Gly Lys Tyr Tyr Gly Lys Ala Lys Lys Tyr Tyr Lys Tyr Lys
         35                  40                  45
```

-continued

Asn Ser Gly Lys Tyr Lys Tyr Leu Lys Ala Arg Lys Tyr His Arg
    50                  55                  60

Lys Gly Tyr Lys Lys Tyr Gly Gly Gly Ser Ser
65                  70                  75

<210> SEQ ID NO 6
<211> LENGTH: 10
<212> TYPE: PRT
<213> ORGANISM: Artificial Sequence
<220> FEATURE:
<223> OTHER INFORMATION: fragment sequence derived from FP-1

<400> SEQUENCE: 6

Ala Lys Pro Ser Tyr Pro Pro Thr Tyr Lys
1               5                   10

<210> SEQ ID NO 7
<211> LENGTH: 565
<212> TYPE: PRT
<213> ORGANISM: Artificial Sequence
<220> FEATURE:
<223> OTHER INFORMATION: FP-1

<400> SEQUENCE: 7

Met Glu Gly Ile Lys Leu Asn Leu Cys Leu Leu Cys Ile Phe Thr Phe
1               5                   10                  15

Asp Val Leu Gly Phe Ser Asn Gly Asn Ile Tyr Asn Ala His Val Ser
            20                  25                  30

Ser Tyr Ala Gly Ala Ser Ala Gly Ala Tyr Lys Lys Leu Pro Asn Ala
        35                  40                  45

Tyr Pro Tyr Gly Thr Lys Pro Glu Pro Val Tyr Lys Pro Val Lys Thr
    50                  55                  60

Ser Tyr Ser Ala Pro Tyr Lys Pro Pro Thr Tyr Gln Gln Leu Lys Lys
65                  70                  75                  80

Lys Val Asp Tyr Arg Pro Thr Lys Ser Tyr Pro Pro Thr Tyr Gly Ser
                85                  90                  95

Lys Thr Asn Tyr Leu Pro Leu Ala Lys Lys Leu Ser Ser Tyr Lys Pro
            100                 105                 110

Ile Lys Thr Thr Tyr Asn Ala Lys Thr Asn Tyr Pro Pro Val Tyr Lys
        115                 120                 125

Pro Lys Met Thr Tyr Pro Thr Tyr Lys Pro Lys Pro Ser Tyr Pro
    130                 135                 140

Pro Thr Tyr Lys Ser Lys Pro Thr Tyr Lys Pro Lys Ile Thr Cys Pro
145                 150                 155                 160

Pro Thr Tyr Lys Ala Lys Pro Ser Tyr Pro Thr Tyr Lys Pro Lys
                165                 170                 175

Lys Thr Tyr Pro Pro Thr Tyr Lys Pro Lys Val Thr Tyr Pro Pro Thr
            180                 185                 190

Tyr Lys Pro Lys Pro Ser Tyr Pro Ile Tyr Lys Ser Lys Pro Thr
        195                 200                 205

Tyr Lys Pro Lys Ile Thr Tyr Pro Thr Tyr Lys Ala Lys Pro Ser
    210                 215                 220

Tyr Pro Pro Thr Tyr Lys Ala Lys Pro Ser Pro Pro Thr Tyr Lys
225                 230                 235                 240

Ala Lys Pro Thr Tyr Lys Ala Lys Pro Thr Tyr Pro Ser Thr Tyr Lys
                245                 250                 255

Ala Lys Pro Thr Tyr Pro Pro Thr Tyr Lys Ala Lys Pro Ser Tyr Pro

```
                    260                 265                 270
Pro Thr Tyr Lys Ala Lys Pro Ser Tyr Pro Thr Tyr Lys Ala Lys
            275                 280                 285
Pro Thr Tyr Ile Ala Lys Pro Ser Tyr Pro Thr Tyr Lys Ala Lys
            290                 295                 300
Pro Ser Tyr Pro Pro Thr Tyr Lys Ala Lys Pro Ser Tyr Pro Thr
305                 310                 315                 320
Tyr Lys Ala Lys Ser Ser Tyr Pro Pro Thr Tyr Lys Ala Lys Pro Thr
            325                 330                 335
Tyr Lys Ala Lys Pro Thr Tyr Pro Ser Thr Tyr Lys Ala Lys Pro Ser
            340                 345                 350
Tyr Pro Pro Thr Tyr Lys Ala Lys Pro Thr Tyr Lys Ala Lys Pro Thr
            355                 360                 365
Tyr Pro Ser Thr Tyr Lys Ala Lys Pro Tyr Pro Ser Thr Tyr Lys
            370                 375                 380
Ala Lys Pro Ser Tyr Pro Pro Thr Tyr Lys Pro Lys Ile Ser Tyr Pro
385                 390                 395                 400
Pro Thr Tyr Lys Ala Lys Pro Ser Tyr Pro Ser Thr Tyr Lys Ala Lys
            405                 410                 415
Ser Ser Tyr Pro Pro Thr Tyr Lys Ala Lys Pro Ser Tyr Pro Pro Thr
            420                 425                 430
Tyr Lys Ala Lys Pro Thr Tyr Lys Ala Lys Pro Thr Tyr Pro Ser Thr
            435                 440                 445
Tyr Lys Ala Lys Pro Thr Tyr Lys Ala Lys Pro Thr Tyr Pro Pro Thr
            450                 455                 460
Tyr Lys Ala Lys Pro Ser Tyr Pro Pro Thr Tyr Lys Pro Lys Pro Ser
465                 470                 475                 480
Tyr Pro Pro Thr Tyr Lys Ser Lys Ser Ser Tyr Pro Ser Ser Tyr Lys
            485                 490                 495
Pro Lys Lys Thr Tyr Pro Pro Thr Tyr Lys Pro Lys Leu Thr Tyr Pro
            500                 505                 510
Pro Thr Tyr Lys Pro Lys Pro Ser Tyr Pro Pro Ser Tyr Lys Pro Lys
            515                 520                 525
Ile Thr Tyr Pro Ser Thr Tyr Lys Leu Lys Pro Ser Tyr Pro Pro Thr
            530                 535                 540
Tyr Lys Ser Lys Thr Ser Tyr Pro Pro Thr Tyr Asn Lys Lys Ile Ser
545                 550                 555                 560
Tyr Pro Ser Gln Tyr
            565

<210> SEQ ID NO 8
<211> LENGTH: 3
<212> TYPE: PRT
<213> ORGANISM: Artificial Sequence
<220> FEATURE:
<223> OTHER INFORMATION: RGD Group 1

<400> SEQUENCE: 8

Arg Gly Asp
  1

<210> SEQ ID NO 9
<211> LENGTH: 4
<212> TYPE: PRT
<213> ORGANISM: Artificial Sequence
<220> FEATURE:
<223> OTHER INFORMATION: RGD Group 2
```

```
<400> SEQUENCE: 9

Arg Gly Asp Ser
 1

<210> SEQ ID NO 10
<211> LENGTH: 4
<212> TYPE: PRT
<213> ORGANISM: Artificial Sequence
<220> FEATURE:
<223> OTHER INFORMATION: RGD Group 3

<400> SEQUENCE: 10

Arg Gly Asp Cys
 1

<210> SEQ ID NO 11
<211> LENGTH: 4
<212> TYPE: PRT
<213> ORGANISM: Artificial Sequence
<220> FEATURE:
<223> OTHER INFORMATION: RGD Group 4

<400> SEQUENCE: 11

Arg Gly Asp Val
 1

<210> SEQ ID NO 12
<211> LENGTH: 10
<212> TYPE: PRT
<213> ORGANISM: Artificial Sequence
<220> FEATURE:
<223> OTHER INFORMATION: RGD Group 5

<400> SEQUENCE: 12

Arg Gly Asp Ser Pro Ala Ser Ser Lys Pro
 1               5                  10

<210> SEQ ID NO 13
<211> LENGTH: 5
<212> TYPE: PRT
<213> ORGANISM: Artificial Sequence
<220> FEATURE:
<223> OTHER INFORMATION: RGD Group 6

<400> SEQUENCE: 13

Gly Arg Gly Asp Ser
 1               5

<210> SEQ ID NO 14
<211> LENGTH: 6
<212> TYPE: PRT
<213> ORGANISM: Artificial Sequence
<220> FEATURE:
<223> OTHER INFORMATION: RGD Group 7

<400> SEQUENCE: 14

Gly Arg Gly Asp Thr Pro
 1               5

<210> SEQ ID NO 15
<211> LENGTH: 6
<212> TYPE: PRT
<213> ORGANISM: Artificial Sequence
<220> FEATURE:
<223> OTHER INFORMATION: RGD Group 8
```

```
<400> SEQUENCE: 15

Gly Arg Gly Asp Ser Pro
 1               5

<210> SEQ ID NO 16
<211> LENGTH: 7
<212> TYPE: PRT
<213> ORGANISM: Artificial Sequence
<220> FEATURE:
<223> OTHER INFORMATION: RGD Group 9

<400> SEQUENCE: 16

Gly Arg Gly Asp Ser Pro Cys
 1               5

<210> SEQ ID NO 17
<211> LENGTH: 5
<212> TYPE: PRT
<213> ORGANISM: Artificial Sequence
<220> FEATURE:
<223> OTHER INFORMATION: RGD Group 10

<400> SEQUENCE: 17

Tyr Arg Gly Asp Ser
 1               5

<210> SEQ ID NO 18
<211> LENGTH: 273
<212> TYPE: PRT
<213> ORGANISM: Streptomyces antibioticus
<220> FEATURE:
<221> NAME/KEY: PEPTIDE
<222> LOCATION: (1)..(273)
<223> OTHER INFORMATION: Tyrosinase

<400> SEQUENCE: 18

Met Thr Val Arg Lys Asn Gln Ala Ser Leu Thr Ala Glu Glu Lys Arg
 1               5                  10                  15

Arg Phe Val Ala Ala Leu Leu Glu Leu Lys Arg Thr Gly Arg Tyr Asp
                20                  25                  30

Ala Phe Val Thr Thr His Asn Ala Phe Ile Leu Gly Asp Thr Asp Asn
            35                  40                  45

Gly Glu Arg Thr Gly His Arg Ser Pro Ser Phe Leu Pro Trp His Arg
        50                  55                  60

Arg Phe Leu Leu Glu Phe Glu Arg Ala Leu Gln Ser Val Asp Ala Ser
 65                  70                  75                  80

Val Ala Leu Pro Tyr Trp Asp Trp Ser Ala Asp Arg Ser Thr Arg Ser
                85                  90                  95

Ser Leu Trp Ala Pro Asp Phe Leu Gly Gly Thr Gly Arg Ser Arg Asp
               100                 105                 110

Gly Gln Val Met Asp Gly Pro Phe Ala Ala Ser Ala Gly Asn Trp Pro
           115                 120                 125

Ile Asn Val Arg Val Asp Gly Arg Thr Phe Leu Arg Arg Ala Leu Gly
       130                 135                 140

Ala Gly Val Ser Glu Leu Pro Thr Arg Ala Glu Val Asp Ser Val Leu
145                 150                 155                 160

Ala Met Ala Thr Tyr Asp Met Ala Pro Trp Asn Ser Gly Ser Asp Gly
               165                 170                 175

Phe Arg Asn His Leu Glu Gly Trp Arg Gly Val Asn Leu His Asn Arg
           180                 185                 190
```

```
Val His Val Trp Val Gly Gly Gln Met Ala Thr Gly Val Ser Pro Asn
            195                 200                 205

Asp Pro Val Phe Trp Leu His His Ala Tyr Ile Asp Lys Leu Trp Ala
        210                 215                 220

Glu Trp Gln Arg Arg His Pro Ser Ser Pro Tyr Leu Pro Gly Gly Gly
225                 230                 235                 240

Thr Pro Asn Val Val Asp Leu Asn Glu Thr Met Lys Pro Trp Asn Asp
                245                 250                 255

Thr Thr Pro Ala Ala Leu Leu Asp His Thr Arg His Tyr Thr Phe Asp
            260                 265                 270

Val
```

<210> SEQ ID NO 19
<211> LENGTH: 21
<212> TYPE: DNA
<213> ORGANISM: Artificial Sequence
<220> FEATURE:
<223> OTHER INFORMATION: forward primer for the amplification of fp-151

<400> SEQUENCE: 19
gaggtatata ttaatgtatc g                                              21

<210> SEQ ID NO 20
<211> LENGTH: 18
<212> TYPE: DNA
<213> ORGANISM: Artificial Sequence
<220> FEATURE:
<223> OTHER INFORMATION: reverse primer for the amplification of fp-151

<400> SEQUENCE: 20
gatttaatct gtatcagg                                                  18

<210> SEQ ID NO 21
<211> LENGTH: 58
<212> TYPE: DNA
<213> ORGANISM: Artificial Sequence
<220> FEATURE:
<223> OTHER INFORMATION: fp-5-HT-forward primer

<400> SEQUENCE: 21
gcccatatga acaccatca ccatcaccat ctggtgccgc gcggcagcag ctctgaag       58

<210> SEQ ID NO 22
<211> LENGTH: 24
<212> TYPE: DNA
<213> ORGANISM: Artificial Sequence
<220> FEATURE:
<223> OTHER INFORMATION: fp-5-HT-reverse primer

<400> SEQUENCE: 22
ttcggatcct cagctgctgc cgcc                                           24

<210> SEQ ID NO 23
<211> LENGTH: 27
<212> TYPE: DNA
<213> ORGANISM: Artificial Sequence
<220> FEATURE:
<223> OTHER INFORMATION: pSA-mel-5p primer

<400> SEQUENCE: 23
caccaggatc cgaccgtccg caagaac                                        27

<210> SEQ ID NO 24

```
<211> LENGTH: 24
<212> TYPE: DNA
<213> ORGANISM: Artificial Sequence
<220> FEATURE:
<223> OTHER INFORMATION: pSA-mel-3p primer

<400> SEQUENCE: 24
cacaagcttt cagacgtcga aggt                                              24

<210> SEQ ID NO 25
<211> LENGTH: 24
<212> TYPE: DNA
<213> ORGANISM: Artificial Sequence
<220> FEATURE:
<223> OTHER INFORMATION: pSA-438-5p primer

<400> SEQUENCE: 25
caccatatgc cggaactcac ccgt                                              24

<210> SEQ ID NO 26
<211> LENGTH: 24
<212> TYPE: DNA
<213> ORGANISM: Artificial Sequence
<220> FEATURE:
<223> OTHER INFORMATION: pSA-438-3p primer

<400> SEQUENCE: 26
cacctcgagt cagttggagg ggaa                                              24

<210> SEQ ID NO 27
<211> LENGTH: 456
<212> TYPE: PRT
<213> ORGANISM: Artificial Sequence
<220> FEATURE:
<223> OTHER INFORMATION: fp-2

<400> SEQUENCE: 27
```

Thr Asn Arg Pro Asp Tyr Asn Asp Asp Glu Glu Asp Asp Tyr Lys Pro
  1               5                  10                  15

Pro Val Tyr Lys Pro Ser Pro Ser Lys Tyr Arg Pro Val Asn Pro Cys
             20                  25                  30

Leu Lys Lys Pro Cys Lys Tyr Asn Gly Val Cys Lys Pro Arg Gly Gly
         35                  40                  45

Ser Tyr Lys Cys Phe Cys Lys Gly Gly Tyr Gly Tyr Asn Cys Asn
     50                  55                  60

Leu Lys Asn Ala Cys Lys Pro Asn Gln Cys Lys Asn Lys Ser Arg Cys
 65                  70                  75                  80

Val Pro Val Gly Lys Thr Phe Lys Cys Val Cys Arg Asn Gly Asn Phe
                 85                  90                  95

Gly Arg Leu Cys Glu Lys Asn Val Cys Ser Pro Asn Pro Cys Lys Asn
            100                 105                 110

Asn Gly Lys Cys Ser Pro Leu Gly Lys Thr Gly Tyr Lys Cys Thr Cys
        115                 120                 125

Ser Gly Gly Tyr Thr Gly Pro Arg Cys Glu Val His Ala Cys Lys Pro
    130                 135                 140

Asn Pro Cys Lys Asn Lys Gly Arg Cys Phe Pro Asp Gly Lys Thr Gly
145                 150                 155                 160

Tyr Lys Cys Arg Cys Val Asp Gly Tyr Ser Gly Pro Thr Cys Gln Glu
                165                 170                 175

Asn Ala Cys Lys Pro Asn Pro Cys Ser Asn Gly Gly Thr Cys Ser Ala
            180                 185                 190

```
Asp Lys Phe Gly Asp Tyr Ser Cys Glu Cys Arg Pro Gly Tyr Phe Gly
        195                 200                 205
Pro Glu Cys Glu Arg Tyr Val Cys Ala Pro Asn Pro Cys Lys Asn Gly
    210                 215                 220
Gly Ile Cys Ser Ser Asp Gly Ser Gly Tyr Arg Cys Arg Cys Lys
225                 230                 235                 240
Gly Gly Tyr Ser Gly Pro Thr Cys Lys Val Asn Val Cys Lys Pro Thr
                245                 250                 255
Pro Cys Lys Asn Ser Gly Arg Cys Val Asn Lys Gly Ser Ser Tyr Asn
            260                 265                 270
Cys Ile Cys Lys Gly Gly Tyr Ser Gly Pro Thr Cys Gly Glu Asn Val
            275                 280                 285
Cys Lys Pro Asn Pro Cys Gln Asn Arg Gly Arg Cys Tyr Pro Asp Asn
        290                 295                 300
Ser Asp Asp Gly Phe Lys Cys Arg Cys Val Gly Gly Tyr Lys Gly Pro
305                 310                 315                 320
Thr Cys Glu Asp Lys Pro Asn Pro Cys Asn Thr Lys Pro Cys Lys Asn
                325                 330                 335
Gly Gly Lys Cys Asn Tyr Asn Gly Lys Ile Tyr Thr Cys Lys Cys Ala
            340                 345                 350
Tyr Gly Trp Arg Gly Arg His Cys Thr Asp Lys Ala Tyr Lys Pro Asn
            355                 360                 365
Pro Cys Val Val Ser Lys Pro Cys Lys Asn Arg Gly Lys Cys Ile Trp
        370                 375                 380
Asn Gly Lys Ala Tyr Arg Cys Lys Cys Ala Tyr Gly Tyr Gly Gly Arg
385                 390                 395                 400
His Cys Thr Lys Lys Ser Tyr Lys Lys Asn Pro Cys Ala Ser Arg Pro
                405                 410                 415
Cys Lys Asn Arg Gly Lys Cys Thr Asp Lys Gly Asn Gly Tyr Val Cys
            420                 425                 430
Lys Cys Ala Arg Gly Tyr Ser Gly Arg Tyr Cys Ser Leu Lys Ser Pro
            435                 440                 445
Pro Ser Tyr Asp Asp Glu Tyr
        450                 455

<210> SEQ ID NO 28
<211> LENGTH: 787
<212> TYPE: PRT
<213> ORGANISM: Artificial Sequence
<220> FEATURE:
<223> OTHER INFORMATION: fp-4

<400> SEQUENCE: 28

Tyr Gly Arg Arg Tyr Gly Glu Pro Ser Gly Tyr Ala Asn Ile Gly His
  1               5                  10                  15
Arg Arg Tyr Tyr Glu Arg Ala Ile Ser Phe His Arg His Ser His Val
             20                  25                  30
His Gly His His Leu Leu His Arg His Val His Arg His Ser Val Leu
         35                  40                  45
His Gly His Val His Met His Arg Val Ser His Arg Ile Met His Arg
     50                  55                  60
His Arg Val Leu His Gly His Val Arg His Arg Val Leu His Arg
 65                  70                  75                  80
His Val His Arg His Arg Val Leu His Gly His Val His Arg His Arg
             85                  90                  95
```

```
Val Leu His Arg His Leu His Arg His Arg Val Leu His Gly His Val
            100                 105                 110

His Arg His Arg Val Leu His Asn His Val His Arg His Ser Val Leu
        115                 120                 125

His Gly His Val His Arg His Arg Val Leu His Arg His Val His Arg
    130                 135                 140

His Asn Val Leu His Gly His Val His Arg His Arg Val Leu His Lys
145                 150                 155                 160

His Val His Asp His Arg Val Leu His Lys His Leu His Lys His Gln
                165                 170                 175

Val Leu His Gly His Val His Arg His Gln Val Leu His Lys His Val
            180                 185                 190

His Asn His Arg Val Leu His Lys His Leu His Lys His Gln Val Leu
        195                 200                 205

His Gly His Val His Thr His Arg Val Leu His Lys His Val His Lys
    210                 215                 220

His Arg Val Leu His Lys His Leu His Lys His Gln Val Leu His Gly
225                 230                 235                 240

His Ile His Thr His Arg Val Leu His Lys His Leu His Lys His Gln
                245                 250                 255

Val Leu His Gly His Val His Thr His Arg Val Leu His Lys His Val
            260                 265                 270

His Lys His Arg Val Leu His Lys His Leu His Lys His Gln Val Leu
        275                 280                 285

His Gly His Val His Met His Arg Val Leu His Lys His Val His Lys
    290                 295                 300

His Arg Val Leu His Lys His Val His Lys His Val Val His Lys
305                 310                 315                 320

His Val His Ser His Arg Val Leu His Lys His Val His Lys His Arg
                325                 330                 335

Val Glu His Gln His Val His Lys His His Val Leu His Arg His Val
            340                 345                 350

His Ser His His Val Val His Ser His Val His Lys His Arg Val Val
        355                 360                 365

His Ser His Val His Lys His Asn Val His Ser His Val His Arg
    370                 375                 380

His Gln Ile Leu His Arg His Val His Arg His Gln Val Val His Arg
385                 390                 395                 400

His Val His Arg His Leu Ile Ala His Arg His Ile His Ser His Gln
                405                 410                 415

Ala Ala Val His Arg His Val His Thr His Val Phe Glu Gly Asn Phe
            420                 425                 430

Asn Asp Asp Gly Thr Asp Val Asn Leu Arg Ile Arg His Gly Ile Ile
        435                 440                 445

Tyr Gly Gly Asn Thr Tyr Arg Leu Ser Gly Gly Arg Arg Arg Phe Met
    450                 455                 460

Thr Leu Trp Gln Glu Cys Leu Glu Ser Tyr Gly Asp Ser Asp Glu Cys
465                 470                 475                 480

Phe Val Gln Leu Gly Asn Gln His Leu Phe Thr Val Val Gln Gly His
                485                 490                 495

His Ser Thr Ser Phe Arg Ser Asp Leu Ser Asn Asp Leu His Pro Asp
            500                 505                 510
```

```
Asn Asn Ile Glu Gln Ile Ala Asn Asp His Val Asn Ile Ala Gln
            515                 520                 525

Ser Thr Asp Gly Asp Ile Asn Asp Phe Ala Asp Thr His Tyr Asn Asp
        530                 535                 540

Val Ala Pro Ile Ala Asp Val His Val Asp Asn Ile Ala Gln Thr Ala
545                 550                 555                 560

Asp Asn His Val Lys Asn Ile Ala Gln Thr Ala His His Val Asn
                565                 570                 575

Asp Val Ala Gln Ile Ala Asp Asp His Val Asn Asp Ile Gly Gln Thr
                580                 585                 590

Ala Tyr Asp His Val Asn Asn Ile Gly Gln Thr Ala Asp Asp His Val
        595                 600                 605

Asn Asp Ile Ala Gln Thr Ala Asp Asp His Val Asn Ala Ile Ala Gln
        610                 615                 620

Thr Ala Asp Asp His Val Asn Ala Ile Ala Gln Thr Ala Asp His Val
625                 630                 635                 640

Asn Asp Ile Gly Asp Thr Ala Asn Ser His Ile Val Arg Val Gln Gly
                645                 650                 655

Val Ala Lys Asn His Leu Tyr Gly Ile Asn Lys Ala Ile Gly Lys His
                660                 665                 670

Ile Gln His Leu Lys Asp Val Ser Asn Arg His Ile Glu Lys Leu Asn
                675                 680                 685

Asn His Ala Thr Lys Asn Leu Leu Gln Ser Ala Leu Gln His Lys Gln
                690                 695                 700

Gln Thr Ile Glu Arg Glu Ile Gln His Lys Arg His Leu Ser Glu Lys
705                 710                 715                 720

Glu Asp Ile Asn Leu Gln His Glu Asn Ala Met Lys Ser Lys Val Ser
                725                 730                 735

Tyr Asp Gly Pro Val Phe Asn Glu Lys Val Ser Val Ser Asn Gln
                740                 745                 750

Gly Ser Tyr Asn Glu Lys Val Pro Val Leu Ser Asn Gly Gly Tyr
                755                 760                 765

Asn Gly Lys Val Ser Ala Leu Ser Asp Gln Gly Ser Tyr Asn Glu Gly
770                 775                 780

Tyr Ala Tyr
785

<210> SEQ ID NO 29
<211> LENGTH: 99
<212> TYPE: PRT
<213> ORGANISM: Artificial Sequence
<220> FEATURE:
<223> OTHER INFORMATION: fp-6

<400> SEQUENCE: 29

Gly Gly Gly Asn Tyr Arg Gly Tyr Cys Ser Asn Lys Gly Cys Arg Ser
1               5                   10                  15

Gly Tyr Ile Phe Tyr Asp Asn Arg Gly Phe Cys Lys Tyr Gly Ser Ser
                20                  25                  30

Ser Tyr Lys Tyr Asp Cys Gly Asn Tyr Ala Gly Cys Cys Leu Pro Arg
            35                  40                  45

Asn Pro Tyr Gly Arg Val Lys Tyr Tyr Cys Thr Lys Lys Tyr Ser Cys
        50                  55                  60

Pro Asp Asp Phe Tyr Tyr Tyr Asn Asn Lys Gly Tyr Tyr Tyr Tyr Asn
65                  70                  75                  80
```

```
Asp Lys Asp Tyr Phe Asn Cys Gly Ser Tyr Asn Gly Cys Cys Leu Arg
            85                  90                  95
Ser Gly Tyr

<210> SEQ ID NO 30
<211> LENGTH: 69
<212> TYPE: DNA
<213> ORGANISM: Artificial Sequence
<220> FEATURE:
<223> OTHER INFORMATION: fp-5h-forward primer

<400> SEQUENCE: 30
gaattcatta agaggagaa attaactatg aaacaccatc accatcacca tctggtgccg        60
cgcggcagc                                                               69

<210> SEQ ID NO 31
<211> LENGTH: 39
<212> TYPE: DNA
<213> ORGANISM: Artificial Sequence
<220> FEATURE:
<223> OTHER INFORMATION: fp-5h-reverse primer

<400> SEQUENCE: 31
aagcttttat tagctgctgc cgccataata tttttata                               39

<210> SEQ ID NO 32
<211> LENGTH: 50
<212> TYPE: DNA
<213> ORGANISM: Artificial Sequence
<220> FEATURE:
<223> OTHER INFORMATION: fp-3h-forward primer

<400> SEQUENCE: 32
ccgaattcat taaagaggag aaattaacta tggcggatta ttatggcccg                  50

<210> SEQ ID NO 33
<211> LENGTH: 28
<212> TYPE: DNA
<213> ORGANISM: Artificial Sequence
<220> FEATURE:
<223> OTHER INFORMATION: fp-3h-reverse primer

<400> SEQUENCE: 33
cgcgaagctt tcagtggtgg tggtggtg                                          28
```

METHOD FOR IN VIVO RESIDUE-SPECIFIC DOPA INCORPORATION INTO MUSSEL ADHESIVE PROTEINS

CROSS-REFERENCE TO RELATED APPLICATION

This application claims priority to and the benefit of Korean Patent Application No. 10-2012-0070246 filed in the Korea Intellectual Property Office on Jun. 28, 2012, the entire contents of which are incorporated herein by reference.

BACKGROUND OF THE INVENTION (a) Field of the Invention

The present invention relates to a method for incorporating 3,4-dihydroxyphenyl-L-alanine (DOPA) into mussel adhesive protein, more particularly, to a method for producing DOPA-incorporated mussel adhesive protein comprising the steps of transforming tyrosine auxotroph so as to express mussel adhesive protein, and culturing the transformant in a DOPA-containing medium to express mussel adhesive protein.

(b) Description of the Related Art

Mussels, one of marine organisms, have been studied as a potential source of water-resistant bioadhesives as they produce and secrete specialized water-resistant adhesive protein, adhere tightly to solid surfaces such as rock underwater and are not influenced by wave impact or buoyancy of seawater. They adhere tightly to surfaces underwater using byssus secreted from the foot. At the end of each thread is an adhesive plaque containing water-resistant glue that enables the plaque to anchor to wet solid surfaces. Mussel adhesive proteins are known as a strong natural adhesive, and they exhibit about two times higher tensile strength than epoxy resin while having flexibility, compared to chemically synthesized adhesive. Mussel adhesive proteins can adhere to various surfaces such as plastics, glass, metal, Teflon and biomaterials, and the like, and they can be applied in medical fields such as adhesion of biotissues at surgery or adhesion of broken tooth, and the like, as they are non-toxic to human body and do not cause immune response. And, they are environmentally friendly as they are biodegradable.

Mussel adhesive proteins consist of 6 kinds of proteins, fp(foot protein)-1 to fp-6. Most of them contain high content of DOPA(3,4-dihydroxyphenyl-L-alanine) that is derived in the hydroxylation process of tyrosine residues, and in fp-3 and fp-5 adjacent to the adhesion side, DOPA residue content are confirmed to be highest. To the contrary, DOPA residue-deficient mussel adhesive protein analogues are known to have significantly reduced adhesion, and thus, it is assumed that DOPA performs a main function for adhesion to surfaces. And, DOPA residues are converted into DOPA o-quinone through an oxidation process, and the DOPA o-quinone causes cross-linking between adhesion proteins, thereby functioning for achieving strong adhesion and keeping adhesive proteins from being dissolved even underwater. Thus, DOPA residue content of mussel adhesive protein is closely related to adhesion property.

Currently, to obtain 1 g of naturally extracted adhesive material from mussels, about 10,000 mussels are required. Thus, despite mussel adhesive proteins have excellent properties, there are many limitations in the industrial use of naturally extracted mussel adhesive proteins. Particularly, fp-5 is expected to be applied as a strong surface adhesive as it exhibits highest DOPA content of 25 mol %, however, it is substantially impossible to obtain the amount for commercialization through extraction. Alternatively, studies on mass production of mussel adhesive proteins using gene recombination technology have been conducted, and it has been confirmed that mussel adhesive protein fp-5 containing 6×-Histidine can be mass-produced in E. coli, and can be separated and purified through Ni-NTA (Biofouling Vol. 27, No. 7, August 2011, 729-737 "Recombinant mussel adhesive protein fp-5 (MAP fp-5) as a bulk bioadhesive and surface coating material").

However, since a post-translational modification mechanism does not exist in E. coli, recombinant mussel adhesive proteins mass-produced in E. coli have unmodified amino acid residues unlike naturally extracted mussel adhesive proteins. Thus, mussel adhesive proteins produced in E. coli are subjected to separate enzymatic and chemical treatments so as to modify tyrosine with DOPA. For example, tyrosinase is known to be a representative enzyme for in vitro modification of tyrosine to DOPA or DOPA o-quinone, and tyrosine residues of mussel adhesive proteins produced in E. coli are in vitro modified to DOPA using tyrosinase. However, since this method requires additional reaction, involves high enzyme cost, and exhibits low modification degree, the industrial application is limited in terms of efficiency and economical feasibility.

Accordingly, there is a demand for development of technology for incorporating DOPA into mussel adhesive protein.

SUMMARY OF THE INVENTION

Accordingly, the inventors developed a method for incorporating DOPA residues into mussel adhesive protein that is in vivo produced in E. coli cells with high contents (mol %) without conducting a separate in vitro modification reaction, by using a residue-specific unnatural amino acid incorporation method so as to incorporate a large amount of DOPA residues into recombinant mussel adhesive protein that is produced in E. coli. And, they confirmed that the produced mussel adhesive protein can be purified while DOPA residues are incorporated, and exhibits much higher DOPA contents compared to the existing mussel adhesive protein that is in vitro modified, and completed the invention.

Thus, the present invention provides a method for producing recombinant mussel adhesive protein wherein tyrosine residues are substituted by DOPA.

The present invention also provides recombinant mussel adhesive protein prepared by the above method, wherein tyrosine residues are substituted by DOPA.

The present invention also provides a transformant wherein an expression vector for mussel adhesive protein is introduced in tyrosine auxotroph.

DETAILED DESCRIPTION OF THE EMBODIMENTS

During repeated studies on the incorporation of unnatural amino acid DOPA instead of tyrosine residues of mussel adhesive protein, the inventors confirmed that if recombinant mussel adhesive protein is expressed in the presence of DOPA using tyrosine auxotroph, DOPA may be incorporated into mussel adhesive protein with high contents, and completed the invention.

A method for incorporation of unnatural amino acids into protein is being developed in the field of biotechnology, and is useful for incorporating new functional groups into protein to produce biomolecules having new properties, and studying the structure and function of protein and interaction between proteins. Methods of incorporation of unnatural amino acid into protein are largely classified into two methods, a site-specific unnatural amino acid incorporation method which is referred to as expanding the genetic code, and a residue-specific unnatural amino acid incorporation method which is referred to as engineering the genetic code.

The site-specific incorporation method newly makes a specific tRNA and codon pair for unnatural amino acid. As the new codon for unnatural amino acid, an amber codon, of which utilization rate is low among stop codons, is largely used, and a quadruplet codon consisting of 4 bases is also used. Since a new codon is used, genetic engineering is required to introduce a new codon into a position where unnatural amino acid is to be incorporated. New tRNA corresponding to new codon is required, and an aminoacyl-tRNA synthetase for connecting unnatural amino acid to new tRNA is also required. The new tRNA and the aminoacyl-tRNA synthetase should be an orthogonal tRNA and aminoacyl-tRNA synthetase pair without a cross reaction between endogenous tRNA and aminoacyl-tRNA synthetase. For this, the aminoacyl-tRNA synthetase is mostly derived from different organism, and it should be expressed together with protein to be produced and new tRNA. The site-specific incorporation method has advantages in that utilization of other natural amino acids in protein synthesis is not disturbed, while it has disadvantages in that additional genetic engineering is required and the method is complicated, and it is difficult to incorporate two or more unnatural amino acids into one protein.

Meanwhile, a residue-specific incorporation method does not require additional genetic engineering unlike a site-specific incorporation method. An amino acid auxotroph is used as an expression host, unnatural amino acid is introduced instead of natural amino acid required for the auxotroph, and the unnatural amino acid is introduced into protein to be expressed. The method has disadvantages in that since an aminoacyl-tRNA synthetase should recognize unnatural amino acid, the unnatural amino acid to be incorporated should have very similar structure to corresponding natural amino acid, and the corresponding natural amino acid cannot be used for protein synthesis, while it has advantages in that since unnatural amino acid is incorporated instead of one natural amino acid, mass incorporation of unnatural amino acids is enabled.

The present invention provide a technology of producing mussel adhesive protein wherein DOPA or DOPA o-quinine is incorporated instead of tyrosine residues with high yield using tyrosine auxotroph.

According to one embodiment, the present invention relates to a method for producing recombinant mussel adhesive protein wherein tyrosine residues are modified with DOPA or DOPA o-quinone.

Specifically, the present invention provides a method for producing recombinant mussel adhesive protein wherein tyrosine residues are substituted by DOPA or DOPA o-quinone, comprising the steps of:

(1) introducing a vector that comprises nucleic acid encoding mussel adhesive protein in tyrosine auxotroph to prepare a transformant;

(2) culturing the prepared transformant in a tyrosine-free medium to a stationary phase; and (3) when the cells become a stationary phase, adding DOPA (3,4-dihydroxyphenylalanine) or DOPA o-quinone to the medium, and additionally culturing.

The present invention also relates to a transformant prepared by transforming tyrosine auxotroph with a vector that comprises nucleic acid encoding the mussel adhesive protein.

Hereinafter, the present invention will be explained according to steps in detail.

The mussel adhesive protein of the present invention is adhesive protein derived from mussel, and preferably, includes mussel adhesive protein derived from *Mytilus edulis*, *Mytilus galloprovincialis* or *Mytilus coruscus*, or a variant thereof, but is not limited thereto. For example, the mussel adhesive protein of the present invention includes protein selected from the group consisting of fp(foot protein)-1 (SEQ ID NO: 7), fp-2 (SEQ ID NO: 27), fp-3 (SEQ ID NO: 4), fp-4 (SEQ ID NO: 28), fp-5 (SEQ ID NO: 5), and fp-6 (SEQ ID NO: 29) respectively derived from the above mussel species, fusion protein including two or more connected proteins, or a variant thereof, and preferably, includes Mefp(*Mytilus edulis* foot protein)-1, Mgfp(*Mytilus galloprovincialis* foot protein)-1, Mcfp(*Mytilus coruscus* foot protein)-1, Mefp-2, Mefp-3, Mgfp-3 and Mgfp-5, or a variant thereof, but is not limited thereto.

And, the mussel adhesive protein preferably includes all mussel adhesive proteins described in WO2006/107183A1 or WO2005/092920. Preferably, the mussel adhesive protein may include Mgfp-3 consisting of an amino acid sequence as shown in SEQ ID NO: 4, Mgfp-5 consisting of an amino acid sequence as shown in SEQ ID NO: 5, or a variant thereof, but is not limited thereto. And, the mussel adhesive protein may include fp-1 fragment consisting of an amino acid sequence as shown in SEQ ID NO: 6, or polypeptide including the fp-1 fragment tandemly repeated 1 to 10 times. And, the mussel adhesive protein may include fusion polypeptide including at least two kinds selected from the group consisting of fp-1 (SEQ ID NO: 7), fp-2 (SEQ ID NO: 27), fp-3 (SEQ ID NO: 4), fp-4 (SEQ ID NO: 28), fp-5 (SEQ ID NO: 5), fp-6 (SEQ ID NO: 29), and fp-1 fragment(SEQ ID NO: 6) tandemly repeated, for example 1 to 10 times, and preferably, examples of the fusion polypeptide may include fp-151 as shown in SEQ ID NO: 1, and fp-131 as shown in SEQ ID NO: 3, but is not limited thereto.

The variant of the mussel adhesive protein of the present invention may comprise additional sequence at a carboxy- or amino-terminal of the mussel adhesive protein, or some amino acids may be substituted by other amino acids, on the assumption that it preferably maintains adhesion of mussel adhesive protein. More preferably, polypeptide consisting of 3 to 25 amino acids comprising RGD(Arg Gly Asp) may be attached to a carboxy- or amino-terminal of the mussel adhesive protein, or 1 to 100%, preferably 5 to 100% of total number of tyrosine residues constituting the mussel adhesive protein may be substituted by 3,4-dihydroxyphenyl-L-alanine (DOPA).

The 3 to 25 amino acids comprising RGD may be preferably at least one selected from the group consisting of RGD (Arg Gly Asp, SEQ ID NO: 8), RGDS(Arg Gly Asp Ser, SEQ ID NO: 9), RGDC(Arg Gly Asp Cys, SEQ ID NO: 10), RGDV(Arg Gly Asp Val, SEQ ID NO: 11), RGDSPASSKP (Arg Gly Asp Ser Pro Ala Ser Ser Lys Pro, SEQ ID NO: 12), GRGDS(Gly Arg Gly Asp Ser, SEQ ID NO: 13), GRGDTP (Gly Arg Gly Asp Thr Pro, SEQ ID NO: 14), GRGDSP(Gly Arg Gly Asp Ser Pro, SEQ ID NO: 15), GRGDSPC(Gly Arg Gly Asp Ser Pro Cys, SEQ ID NO: 16) and YRGDS(Tyr Arg Gly Asp Ser, SEQ ID NO: 17), but is not limited thereto.

The variant of the mussel adhesive protein wherein polypeptide consisting of 3 to 25 amino acids comprising RGD is attached to a carboxyl- or amino-terminal of the mussel adhesive protein may be preferably fp-151-RGD polypeptide consisting of an amino acid sequence as shown in SEQ ID NO:2, but is not limited thereto.

The nucleic acid encoding mussel adhesive protein, used in the step (1), is preferably inserted in a common vector that is manufactured for expression of foreign genes, and is designed for mass-production by genetic engineering methods, but is not limited thereto. The vector may be appropriately selected according to the kind and characteristics of host cell for production of protein, or it may be newly manufactured.

As used herein, a vector refers to a means for insertion of nucleic acid sequence encoding target protein into a host cell. The vector may include a plasmid vector, a cosmid vector, a viral vector, and the like. A suitable expression vector may comprise expression regulatory elements such as a promoter, an operator, an initiation codon, a stop codon, a polyadenylation signal, and an enhancer, and the like, a signal sequence or a leader sequence for membrane targeting or secretion, and it may be variously manufactured according to purposes. The initiation codon and stop codon are generally considered as a part of a nucleotide sequence encoding target protein, and should exhibit action in individuals when a gene construct is administered, and be in frame with a coding sequence. The promoter of the vector may be constitutive or inducible. And, the expression vector comprises a selective marker for selection of a vector-containing host cell, and if it is a reproducible expression vector, comprises an origin of replication. The vector may be auto replicated or integrated into host genome DNA.

According to specific example of the invention, an expression vector is constructed by inserting nucleic acid encoding mussel adhesive protein into a pQE-80L vector, but is not limited thereto.

And, the nucleic acid sequence encoding mussel adhesive protein may be modified or optimized with a codon mainly used in a host cell, or modified with other codon sequences to avoid overlap or repeat of a codon sequence.

Tyrosine auxotroph is transformed with the constructed vector that comprises a nucleic acid sequence encoding mussel adhesive protein to prepare a transformant.

The tyrosine auxotroph refers to a strain that cannot synthesize tyrosine in cells, to which tyrosine should be supplied from the outside, and it may be a tyrosine auxotrophic mutants of cells having high DNA incorporation efficiency and high expression efficiency of incorporated DNA. For example, the tyrosine auxotroph may be tyrosine auxotrophic mutants of well known eukaryotic and prokaryotic cells such as *Escherichia coli, Pseudomonas, Bacillus, Streptomyces*, fungus, yeast, insect cells such as *Spodoptera frugiperda* (SF9), animal cells such as CHO, COS 1, COS 7, BSC 1, BSC40, BMT 10, and the like. Specifically, it may be *E. coli* tyrosine auxotroph (*E. coli* JW2581 tyrosine auxotroph; yale genetic stock center; http://cgsc.biology.yale.edu/Strain.php?ID=108330).

The transformation of the tyrosine auxotroph with a vector that comprises a nucleic acid sequence encoding mussel adhesive protein may be easily conducted by common methods. The selection and manufacture of the vector, transformation and expression of recombinant protein, and the like may be easily conducted by one of ordinary knowledge in the art, and modifications or variations of common methods is within the scope of the invention.

For insertion of vector into a host cell to prepare a transformant, a calcium phosphate method or a calcium chloride/rubidium chloride method, electroporation, electroinjection, chemical treatment such as PEG, and the like, gene gun, and the like may be used (see, Sambrook, J. et al., Molecular Cloning, A Laboratory Manual(Vol 2), Cold Spring Harbor Laboratory, 1. 74, 1989).

According to specific example of the invention, a vector that comprises a nucleic acid sequence encoding mussel adhesive protein is inserted into *E. coli* auxotrophic mutant by thermal shock at 40 to 45° C., for example at about 42° C. for 60 to 120 seconds, for example, about 90 seconds, to prepare a transformant that produces the modified mussel adhesive protein.

In the step (2), the prepared transformant is cultured in a tyrosine-free medium to a stationary phase. The tyrosine-free medium may be a common medium from which tyrosine has been removed, and preferably, it may be a medium prepared by adding 19 kinds of natural amino acids except tyrosine (alanine, isoleucine, leucine, methionine, phenylalanine, proline, tryptophan, valine, asparagine, cystein, glutamine, glycine, serine, threonine, aspartic acid, glutamic acid, arginine, histidine, and lysine) to minimal medium, for example M9 minimal medium containing calcium chloride, magnesium sulfate, glucose and thiamine.

Culture conditions for culture of the transformant may be appropriately selected according to host cells. Culture temperature, pH of the medium, culture time, and the like may be appropriately controlled for cell growth and mass production of protein. For example, transformed *E. coli* tyrosine auxotroph may be cultured in a M9 minimal medium containing 19 kinds of amino acids except tyrosine, at 35 to 40° C., for example at about 36 to 38° C., to a stationary phase, for example for about 5 to 7 hours.

When the cells reach a stationary phase, DOPA (3,4-dihydroxyphenylalanine) is added to the medium and cultured (step 3). Since tyrosine auxotroph cannot in vivo synthesize tyrosine, protein is synthesized using tyrosine supplied to the medium, and if DOPA (3,4-dihydroxyphenylalanine) having a similar structure to tyrosine is added, DOPA (3,4-dihydroxyphenylalanine) is used instead of tyrosine when synthesizing protein to obtain mussel adhesive protein wherein tyrosine residues are substituted by DOPA. The added amount of DOPA may be 0.1 to 2 mM, specifically 0.5 to 1 mM, but is not limited thereto. If the added amount of DOPA is less than the above range, incorporation rate of DOPA may become lower, and if it is greater than the above range, toxicity may be increased to adversely influence on protein expression. Wherein, expression inducer IPTG (isopropyl-β-D-thiogalactopyranoside) may be added for production of mussel adhesive protein, but not limited thereto.

The culturing in the step (3) may be conducted at 36 to 38° C., for example at about 37° C., to a stationary phase, for example for about 3 hours 30 minutes to 5 hours 30 minutes.

The expression of mussel adhesive protein wherein tyrosine residues are modified with DOPA may be confirmed, for example, on a common SDS-PAGE, by resuspending recovered whole cells in a buffer aqueous solution, disrupting them with an ultrasonicator or a high pressure pulverizer, and dividing the disrupted cells into a soluble fraction and a non-soluble fraction.

And, the method for producing mussel adhesive protein may further comprise the step of (4) separating and purifying recombinant mussel adhesive protein produced in the transformant, wherein tyrosine residues are substituted by DOPA, after the step (3).

For the separation, electrophoresis, centrifugation, gel filtration, precipitation, dialysis, chromatography (ion exchange chromatography, affinity chromatography, immunoadsorption affinity chromatography, reverse phase HPLC, gel filtration HPLC), and the like may be used, but not limited thereto.

The modified mussel adhesive protein that is produced in the transformant may be separated and purified by disrupting recovered whole cells with an ultrasonicator, and then, subjecting a soluble fraction of the disrupted cells to modified affinity chromatography using a nickel resin column. The purified protein may be dialyzed using water to remove remaining water and ingredients other than protein in the protein aqueous solution, and lyophilizing to finally produce purified protein in the form of powder. Meanwhile, modified mussel adhesive protein existing in the non-soluble fraction may be purified by the purification method of mussel adhesive protein. Finally, purification of the modified mussel adhesive protein was confirmed by common SDS-PAGE and MALDI-MS analysis, and modification of the tyrosine residue of mussel adhesive protein was confirmed by amino acid composition analysis(FIG. 2 to FIG. 8).

According to another embodiment of the invention, a transformant prepared by transforming tyrosine auxotroph with a vector that comprises nucleic acid encoding mussel adhesive protein is provided. The tyrosine auxotroph, mussel adhesive protein, and transformation method are as explained above.

According to still another embodiment of the invention, recombinant mussel adhesive protein produced by the above method, wherein tyrosine residues are substituted with DOPA, and an adhesive composition comprising the recombinant mussel adhesive protein are provided.

The recombinant mussel adhesive protein has DOPA incorporation rate in total tyrosine, of 30% or more, or 50% or more, specifically 70% or more, more specifically 80% or more, more specifically 85% or more, for example 90% or more.

The modified mussel adhesive protein of the present invention may be identically applied for use of the existing mussel adhesive protein, and it may maintain effective adhesion to mass adhesion system, for example, metal such as aluminum, and the like, as well as microadhesion system.

The adhesive composition of the present invention may be applied for a substrate selected from the group consisting of plastics, glass, metal and polymer synthetic resin, and it may be used for adhesion or fixation of the substrate. And, the existing mussel adhesive protein adhesive preparation methods may be applied, common adhesive using methods may be applied, and the representative method is coating.

Particularly, the adhesive composition of the present invention may be applied to biomaterials, wherein the biomaterials refer to all animals and plants classified as organisms, and parts derived from the animals and plants, and examples thereof may include cells, tissues, organs, RNA, DNA, proteins, peptides, polynucleotide, hormones, lipids and compounds, but not limited thereto. If applied to biomaterials, the instructions, the amount used, and the form of Cell-Tak product (BD Biosciences, Two oak Park, Bedford, Mass., USA) that is currently commercially available may be applied to the adhesive of the present invention. For example, the adhesive of the present invention may be solvent-based, water soluble, or non-solvent-based, and it may be used to a substrate at 0.01 to 100 ug/cm$^2$, but is not limited thereto.

The applications of the adhesive of the present invention may include (1) adhesion between substrates in water (water or water containing salt); (2) orthopedic treatment such as transplantation of artificial materials and bone, ligament, tendon, meniscus and muscle treatment; (3) ophthalmic adhesion such as treatment of perforation, lacerated wound, incision, and the like, corneal transplantation, insertion of artificial cornea; (4) dental adhesion such as retainer, bridge, installation of crown, fixation of tooth mobility, treatment of broken tooth, and fixation of filler; (5) surgical treatment such as vascular adhesion, cell tissue adhesion, transplantation of artificial materials, wound suture; (6) adhesion in plants such as adhesion of plant grafts, wound healing; and (7) transplantation of drug, hormone, biological factors, medicine, physiological or metabolic observation device, antibiotics and cells (see: U.S. Pat. No. 5,015,677), but not limited thereto.

And, adhesion of the adhesive may be controlled by treating the adhesive with material selected from the group consisting of a surfactant, an oxidant, a crosslinker, and a filler, or controlling the concentration of modified mussel adhesive protein that is an active ingredient of the adhesive (see: U.S. Pat. No. 5,015,677).

THE TECHNICAL EFFECT OF THE INVENTION

According to the present invention, since DOPA residue-incorporated mussel adhesive protein may be directly produced from transformed E. coli without conducting a separate in vitro tyrosine modification, active mussel adhesive protein may be easily secured.

Hereinafter, the present invention will be explained with reference to the following Examples. However, these examples are only to illustrate the invention, and the invention is not limited thereto.

EXAMPLE

Example 1

Construction of Mussel Adhesive Protein fp-5 Expression Vector

Naturally occurring mussel adhesive protein Mgfp-5 genes (Genbank No. AY521220; AAS00463 (mussel adhesive protein Mgfp-5; SEQ ID NO: 5) coding polynucleotide) were expressed in E. coli to obtain recombinant mussel adhesive protein fp-5(SEQ ID NO: 5: see Biofouling Vol. 27, No. 7, August 2011, 729-737 "Recombinant mussel adhesive protein fp-5 (MAP fp-5) as a bulk bioadhesive and surface coating material"). For the specific method, see 'D. S. Hwang et al., Applied and environmental microbiology, 70, 3352-3359, 2004'.

And, to increase the expression amount of the obtained mussel adhesive protein fp-5, the genes (SEQ ID NO: 2(AY521220) were modified with a gene codon frequently used in *E. coli* to chemically synthesize (Biofouling Vol. 27, No. 7, August 2011, 729-737 "Recombinant mussel adhesive protein fp-5 (MAP fp-5) as a bulk bioadhesive and surface coating material"), and PCR-amplified using two primers, fp-5h-forward: 5'-GAA TTC ATT AAA GAG GAG AAA TTA ACT ATG AAA CAC CAT CAC CAT CAC CAT CTG GTG CCG CGC GGC AGC-3' (SEQ ID NO: 30), fp-5h-reverse: 5'-AAG CTT TTA TTA GCT GCT GCC GCC ATA ATA TTT TTT ATA-3' (SEQ ID NO: 31).

Figure 1:
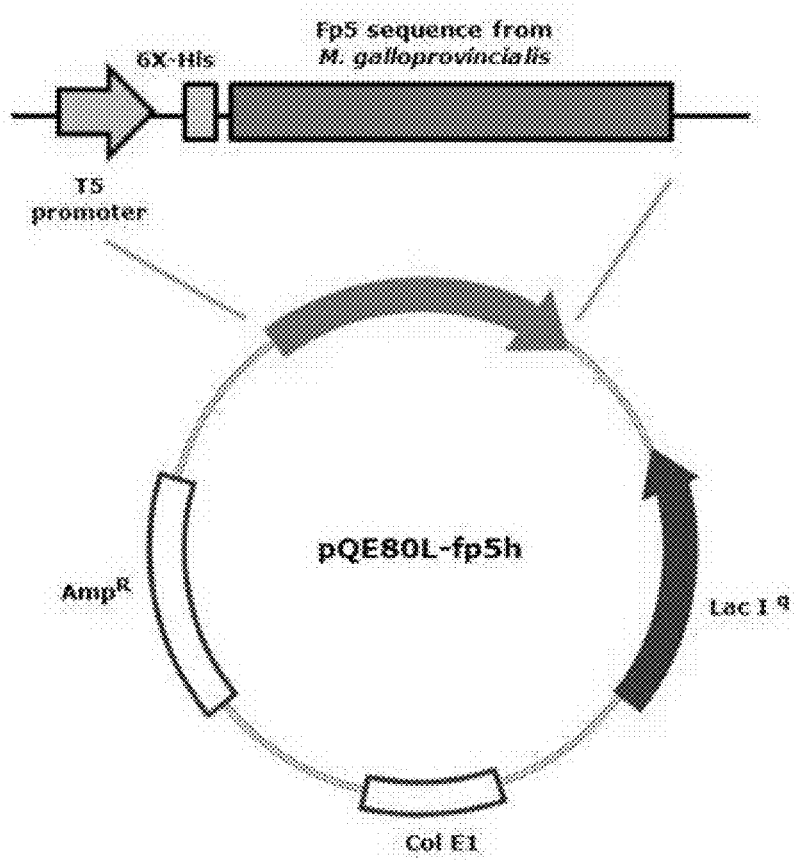
FIG. 1 is a cleavage map of mussel adhesive protein expression vector pQE-80L-fp5h.

The obtained amplification product was inserted into a pQE-80L vector (QIAGEN) using restriction enzyme EcoR I and HindIII site to construct Mgfp-5 inserted recombinant vector (FIG. 1). The constructed recombinant vector was named as pQE-80L-fp5h.

Example 2

Construction of Mussel Adhesive Protein fp-3 Expression Vector

Naturally occurring mussel adhesive protein Mgfp-3 genes were expressed in *E. coli* to obtain recombinant mussel adhesive protein fp-3. And, to increase the expression amount of the obtained mussel adhesive protein fp-3, the genes were modified with a gene codon frequently used in *E. coli* to chemically synthesize, and PCR-amplified using two primers, fp-3h-forward: 5'-CC GAA TTC ATT AAA GAG GAG AAA TTA ACT ATG GCG GAT TAT TAT GGC CCG-3' (SEQ ID NO: 32), fp-3h-reverse: 5'-C GCG AAG CTT TCA GTG GTG GTG GTG GTG-3'(SEQ ID NO: 33). The obtained amplification product was inserted into a pQE-80L vector (QIAGEN) using restriction enzyme EcoR I and HindIII site to construct a Mgfp-3 inserted recombinant vector. The constructed recombinant vector was named as pQE-80L-fp3h.

Example 3

Construction of a Transformant Comprising Mussel Adhesive Protein Expression Vector To construct a transformant expressing mussel adhesive protein, comprising the mussel adhesive protein expression vector pQE-80L-fp5h or pQE-80L-fp3h constructed in the Example 1, the vector pQE-80L-fp5h was subjected to heat shock at 42° C. for 90 seconds to insert into *E. coli* tyrosine auxotroph (*E. coli* JW2581 tyrosine auxotroph; yale genetic stock center; http://cgsc.biology.yale.edu/Strain.php?ID=108330), and selected in an ampicillin added LB-agar medium.

Example 4

Expression of DOPA Residue-Incorporated Mussel Adhesive Protein

In an M9 minimal medium containing M9 salt (a solution of disodium hydrogen phosphate 67.8 g, potassium dihydrogen phosphate 30.0 g, sodium chloride 5.0 g, and ammonium chloride 10.0 g in 1 L distilled water), calcium chloride, magnesium sulfate, glucose, and thiamine (distilled water 650 ml, M9 salt 100 ml, 20% glucose 20 ml, 1M magnesium sulfate 200 ul, 1M calcium chloride 100 ul, thiamine-hydrochloric acid 1 mg), 19 natural amino acids except tyrosine were dissolved at a concentration of 40 mg/L to prepare a tyrosine-free M9 minimal medium.

The transformant prepared in Example 2 (Single Colony) was shake-cultured in 100 mL of common LB medium (USB Corporation) containing 50 µg/mL ampicillin at 37° C. for about 12 hours. To express DOPA residue-incorporated mussel adhesive protein fp-5, 1 L of the above prepared tyrosine-free M9 minimal medium was prepared, and then, cells that were cultured in M9 minimal medium additionally containing 40 mg/L of tyrosine for about 10-12 hours were transferred to 1 L of tyrosine-free M9 minimal medium such that starting absorbance (starting $OD_{600}$) of a culture solution may become about 0.15. Into 1 L of the M9 minimal medium to which *E. coli* transformant cells were transferred, only a small amount of tyrosine (about 0.02-0.025 Mm) was introduced so as to reach stationary phase at a certain level of absorbance (about 0.7-0.8), and then, shake culture was conducted at 37° C. After culturing for about 6 hours, stationary phase was confirmed.

After confirming stationary phase, DOPA (3,4-dihydroxyphenyl-L-alanine) was introduced to the concentration of 1 mM in the medium. After introducing DOPA, inducer IPTG (isopropyl-β-D-thiogalactopyranoside, 1 mM) was added to induce the expression of the above proteins. After adding IPTG, culture was conducted at 37° C. for additional 6 hours. For a positive control, tyrosine was introduced to the concentration of 1 mM instead of DOPA, and the expression of the proteins was induced with IPTG, and for a negative control, nothing was introduced. After culture, the cells were centrifuged at 4000 rpm for 10 minutes, and then, supernatant was removed, and the cells were recovered.

The recovered cells of the mussel adhesive protein fp5h that was expressed after introducing DOPA, positive control, and negative control were analyzed by tricine SDS-PAGE.

Figure 2:
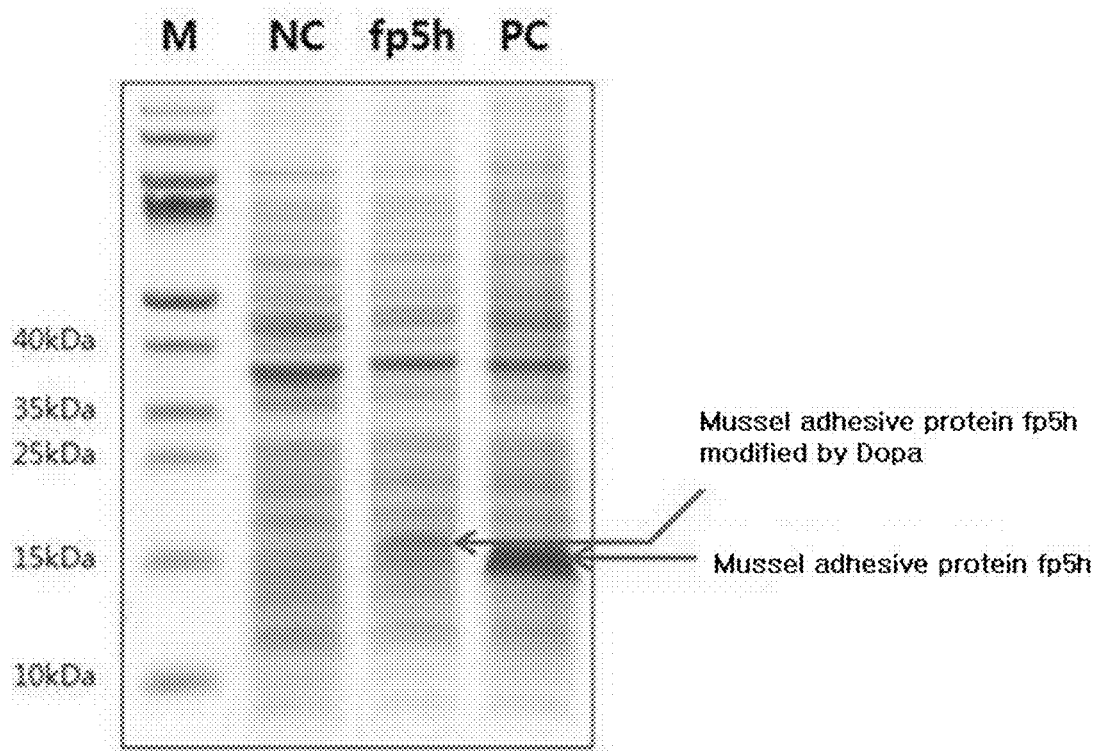
FIG. 2 shows the results of analyzing the whole cells of DOPA-incorporated fp5h that is expressed in a transformant by adding DOPA to an M9 minimal medium, a tyrosine-added positive control, and a negative control where nothing is added, by tricine SDS-PAGE and Coomassie staining.

FIG. 2 is a photo analyzing the whole cells of mussel adhesive protein fp5h expressed in tyrosine auxotroph *E. coli*, positive control (PC), and negative control (NC) by tricine SDS-PAGE and coomassie staining. As shown in FIG. 2, it was confirmed that mussel adhesive protein fp5h was expressed when DOPA was introduced. Compared to tyrosine-introduced positive control, it can be seen that when DOPA was introduced, expression amount decreased and protein band shifted slightly upward, which may be interpreted that the expression amount decreased because protein biosynthesis became difficult due to incorporation of unnatural amino acid DOPA instead of tyrosine, and that the location of protein band was changed because properties of protein such as molecular weight and isoelectric point were changed due to incorporation of DOPA instead of tyrosine in protein.

Figure 3:
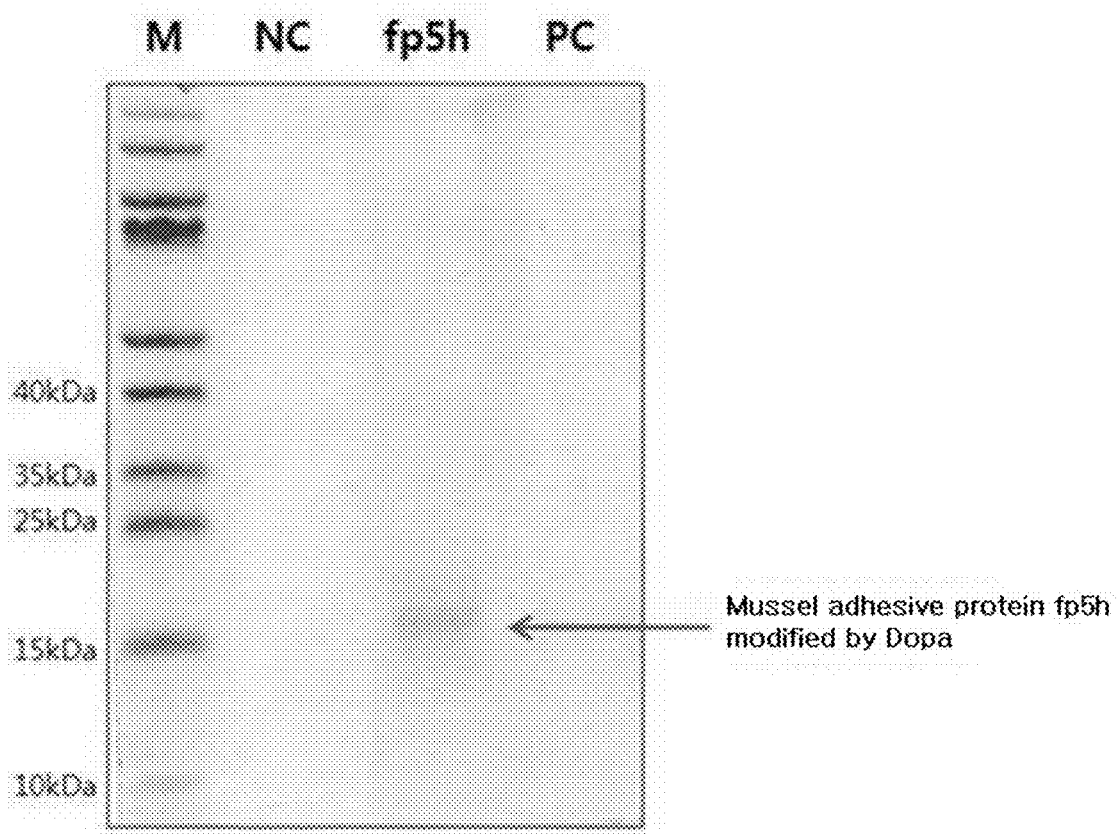
FIG. 3 shows the results of analyzing the whole cells of the DOPA-incorporated fp5h, positive control, and negative control by tricine SDS-PAGE and NBT staining.

FIG. 3 is a photo analyzing by tricine SDS-PAGE and NBT(nitroblue tetrazolium chloride) staining. It is known that if DOPA exists in protein, color change into deep blue occurs by a NBT solution. Seeing that protein band was stained only in DOPA-introduced fp5h, it was confirmed that DOPA residue was successfully incorporated into protein.

Mussel adhesive protein fp3h that was expressed after introducing DOPA was also analyzed by tricine SDS-PAGE.

Figure 4:
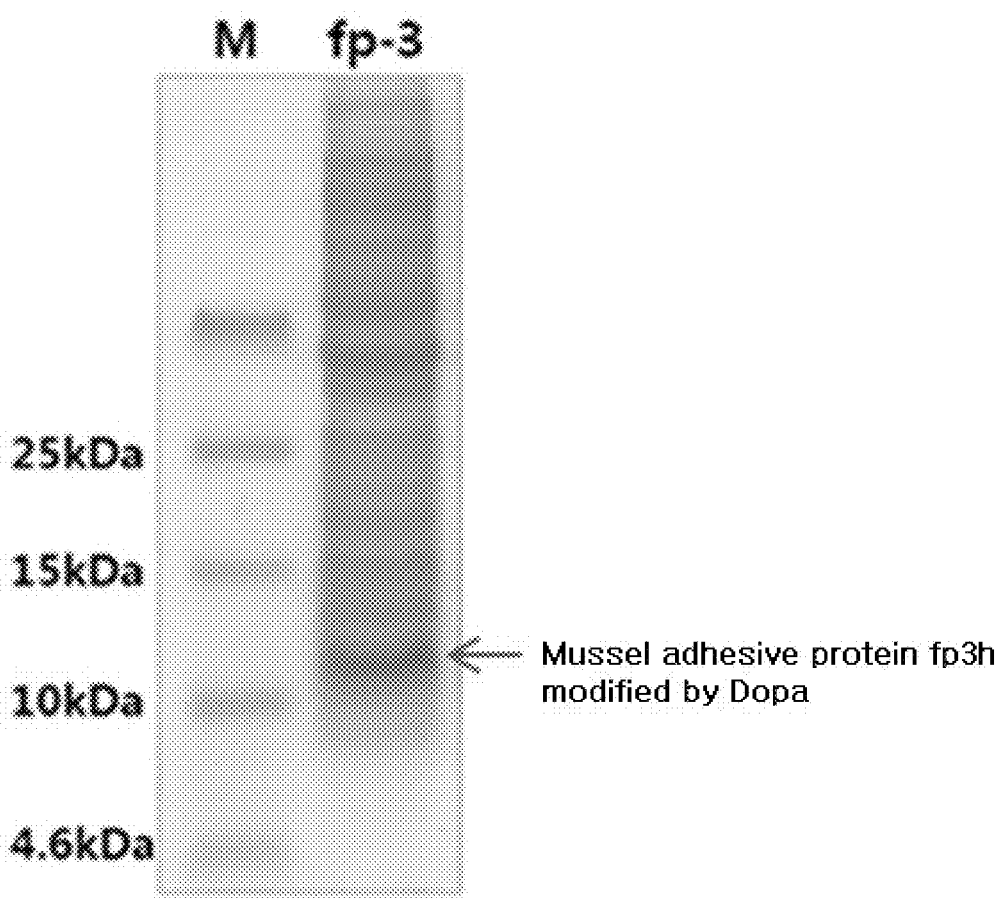
FIG. 4 shows the results of analyzing DOPA-incorporated fp3h that is expressed in a transformant by adding DOPA an M9 minimal medium, with tricine SDS-PAGE and Coomassie staining.

FIG. 4 is a photo analyzing mussel adhesive protein fp3h expressed in tyrosine auxotroph *E. coli* by tricine SDS-PAGE and coomassie staining. As shown in FIG. 4, it was confirmed that mussel adhesive protein fp3h was expressed when DOPA was incorporated.

Figure 5:
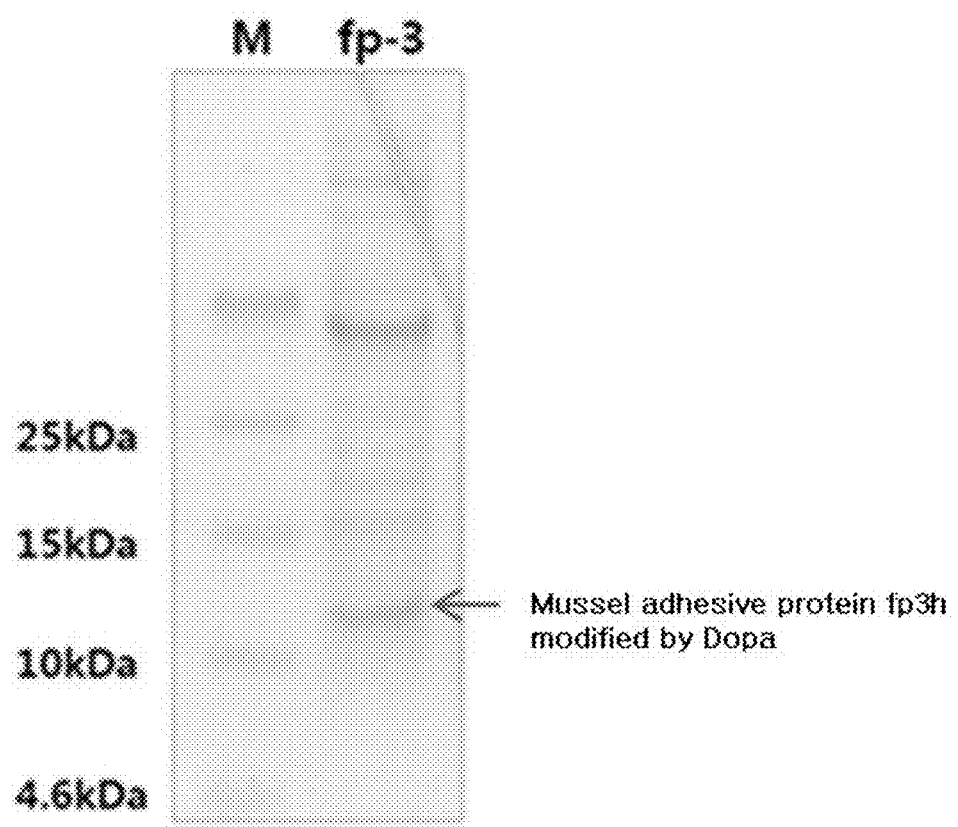
FIG. 5 shows the results of analyzing the DOPA-incorporated fp3h by tricine SDS-PAGE and NBT staining.

FIG. 5 is a photo analyzing by tricine SDS-PAGE and NBT(nitroblue tetrazolium chloride) staining. Seeing that protein band was stained in DOPA-incorporated fp3h, it was confirmed that DOPA residue was successfully incorporated into protein.

Example 5

Purifications of DOPA Residue-Incorporated Mussel Adhesive Proteins fp-5 and fp-3

The DOPA residue-incorporated mussel adhesive protein fp5h was separated and purified by Ni column chromatography. Specifically, the cells that were expressed and then recovered were resuspended in a solution for cell disruption (100 mM sodium phosphate, 10 mM tris, 100 mM boric acid, 10 mM ascorbic acid, 8 M urea, pH ~7), and disrupted using ultrasonicator, and then, the disrupted cells were centrifuged at 9000 rpm for 15 minutes to separate into a soluble fraction (supernatant) and a non-soluble fraction (pellet). Among the separated soluble fraction and non-soluble fraction, the soluble fraction was subjected to a column filled with Nickel agarose resin (Ni-nitrilotriacetic acid (NTA) agarose resin; quiagen) so as to bind protein with the column. Non-bound proteins were washed with a washing solution (100 mM sodium phosphate, 10 mM tris, 100 mM boric acid, 10 mM ascorbic acid, 8 M urea, pH 6.0), and proteins were eluted from the column using 0.5 M HCl. The purified solution was dialyzed using a 5% (v/v) acetic acid solution and water to remove remaining water and ingredients other than protein in the protein aqueous solution, and lyophilized to finally produce purified protein in the form of powder.

Figure 6:
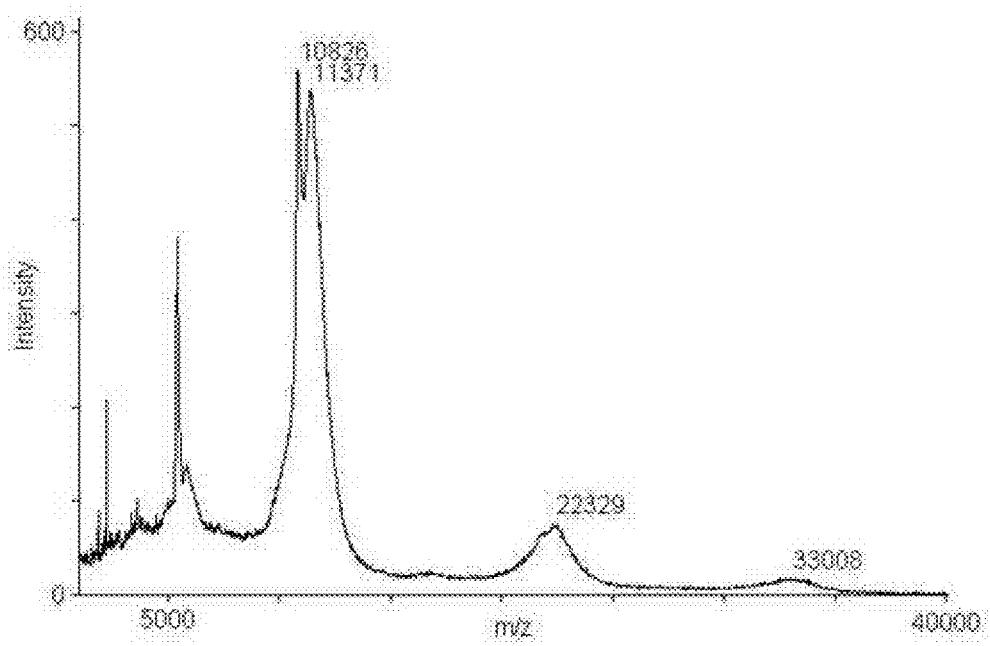
FIG. 6 shows the results of analyzing molecular weight of separated and purified mussel adhesive protein fp5h by MALDI-TOF MS.

FIG. 6 is a graph confirming molecular weight of protein obtained by MALDI-TOF MS analysis (4700 Proteomics Analyzer, Maldi TOF-TOF, Applied Biosystems) of the separated and purified mussel adhesive protein fp5h. As shown in FIG. 4, it was confirmed that DOPA-incorporated mussel adhesive protein may be efficiently purified.

Example 6

Confirmation of DOPA Residue Incorporation in the Produced Mussel Adhesive Protein It was confirmed using an amino acid analyzer whether DOPA residues were incorporated in the separated and purified mussel adhesive protein. About 0.5 mg of the mussel adhesive protein purified in Example 4 was hydrolyzed into amino acid units with 6 M HCl 500 uL, and then, amino acid units constituting protein were qualitatively and quantitatively analyzed using chromatography. About 0.5 mg of protein, 500 uL of a 6 M HCl solution, and 25 uL of phenol were introduced into a glass vial, and argon gas was charged to remove oxygen, and then, the glass vial was heated and sealed. And then, after hydrolyzing at 156° C. for 1 hour, amino acid analysis was conducted. The solution was washed with distilled water and methanol, and evaporated, and then, the protein sample was dissolved in sample buffer, introduced into an Amino acid Analyzer S4300 (SYKAM Company) and analyzed.

Figure 7:
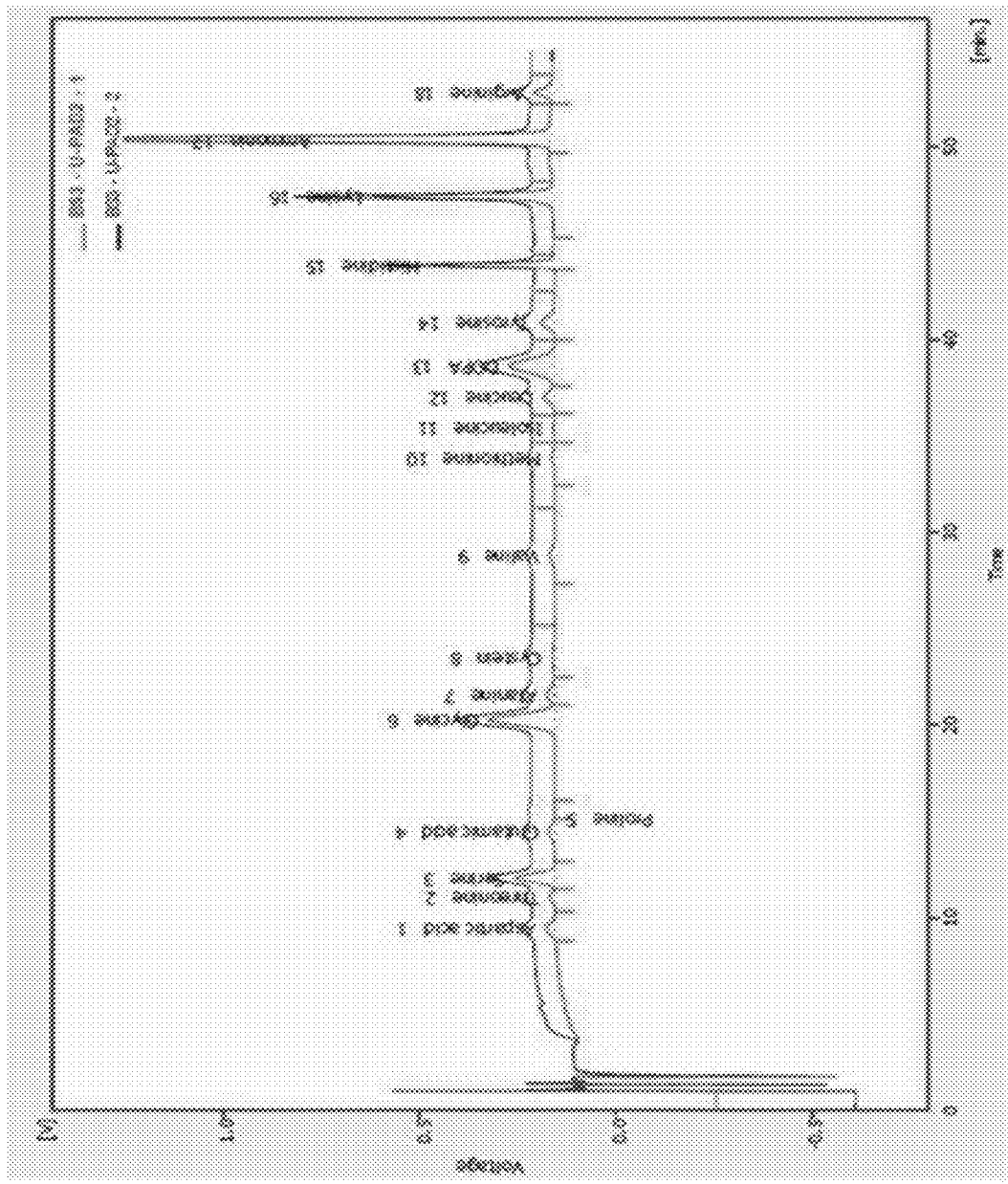
FIG. 7 shows the results of confirming incorporation of DOPA residues by analyzing amino acid composition of separated and purified mussel adhesive protein fp5h with amino acid analyzer.

Table 1 and FIG. 7 respectively show a table and a graph analyzing amino acid units constituting the purified mussel adhesive protein fp5h using the Amino Acid Analyzer. In FIG. 7, U PAD2-1 denotes absorbance at wavelength of 440 nm and is for proline detection, and U PAD2-2 denotes absorbance at 570 nm and is for detection of amino acids other than proline. From the results of Table 1 and FIG. 7, the number of DOPA residues is about 17.8, and thus, it was confirmed that about 1718 DOPA residues were incorporated in total 20 tyrosine sites.

Figure 8:
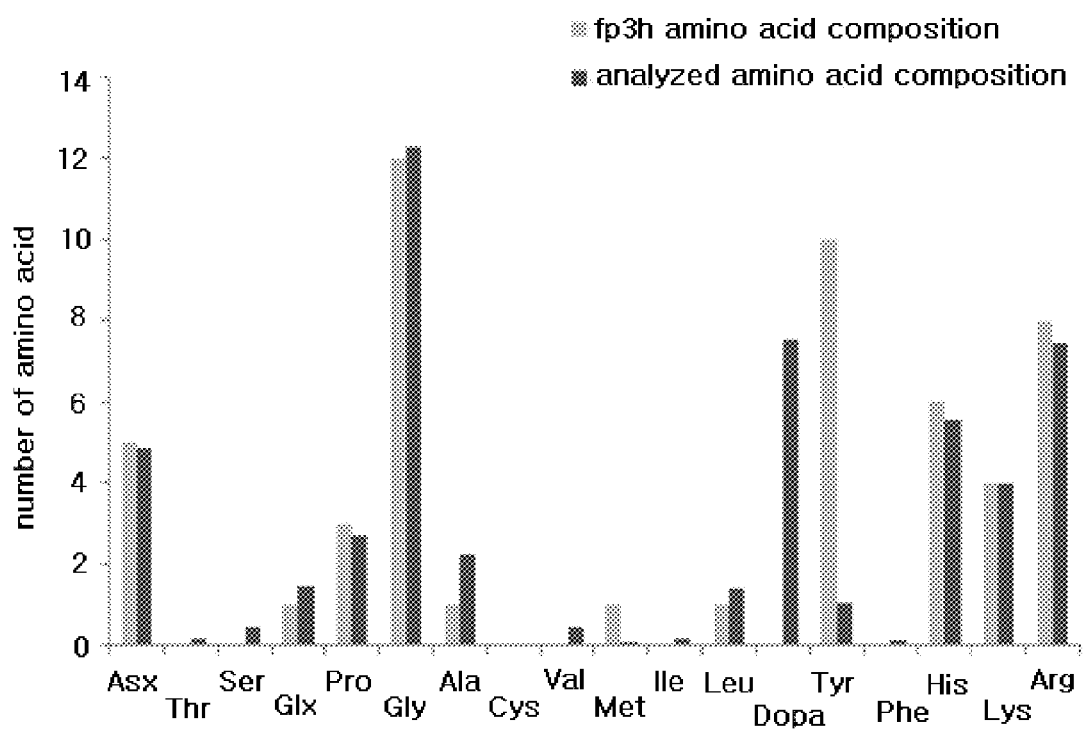
FIG. 8 shows the results of confirming incorporation of DOPA residues by analyzing amino acid composition of separated and purified mussel adhesive protein fp3h with amino acid analyzer.

FIG. 8 is a graph analyzing amino acid units constituting purified mussel adhesive protein fp3h using the Amino Acid Analyzer. As shown in FIG. 8, it was confirmed that about 85~90% tyrosine were substituted by DOPA.

Thus, recombinant mussel adhesive protein wherein about 85~90% tyrosine were substituted by DOPA could be obtained.

TABLE 1

| | Retention time (min) | Response | Amount (nmol/ml) | Amount (%) | # Residue | Compound Name | # Residue |
|---|---|---|---|---|---|---|---|
| 1 | 9.469 | 984.148 | 1.559 | 2.78 | 2.5 | Aspartic acid/ Asparagine | 2 |
| 2 | 11.076 | 546.199 | 0.812 | 1.45 | 1.3 | Threonine | 1 |
| 3 | 12.064 | 2257.72 | 4.762 | 8.48 | 7.5 | Serine | 9 |
| 4 | 14.487 | 945.217 | 1.35 | 2.4 | 2.1 | Glutamic acid/ Glutamine | 2 |
| 5 | 15.11 | 121.534 | 1.485 | 2.64 | 2.3 | Proline | 2 |
| 6 | 20.278 | 7178.592 | 10.639 | 10.94 | 16.9 | Glycine | 16 |
| 7 | 21.564 | 1012.84 | 1.497 | 2.66 | 2.4 | Alanine | 2 |
| 8 | 23.513 | 526.246 | 0.738 | 1.31 | 1.2 | Cystein | 0 |
| 9 | 26.613 | 632.522 | 0.95 | 1.69 | 1.5 | Valine | 1 |
| 10 | 33.856 | 264.851 | 0.422 | 0.75 | 0.7 | Methionine | 1 |
| 11 | 35.433 | 89.322 | 0.144 | 0.26 | 0.2 | Isoleucine | 0 |
| 12 | 37.007 | 1074.377 | 1.609 | 2.06 | 2.6 | Leucine | 2 |
| 13 | 38.633 | 5862.877 | 11.25 | 20.03 | 17.8 | DOPA | |
| 14 | 40.887 | 1403.477 | 2.104 | 3.75 | 3.3 | Tyrosine | 20 |
| 15 | 43.847 | 4293.267 | 6.581 | 11.72 | 10.4 | Histidine | 11 |
| 16 | 47.418 | 8200.666 | 8.583 | 15.28 | 13.6 | Lysine | 17 |
| 17 | 50.229 | 24668.875 | N/A | N/A | N/A | Ammonia | |
| 18 | 62.829 | 1174.049 | 1.688 | 3.01 | 2.7 | Arginine | 3 |
| Total | Total | | 56.173 | 100 | 89 | | 89 |

Example 7

Comparison of DOPA Residue Incorporation Yield

The degree of DOPA residue incorporation using tyrosine auxotroph according to the present invention and the degree of DOPA residue incorporation by the existing tyrosinase co-expression were compared.

7.1. Incorporation of DOPA Residue by Tyrosinase Co-Expression

For expression of active tyrosinase, tyrosinase genes derived from *Streptomyces antibioticus* were PCR-amplified from *Streptomyces antibioticus* genome using two DNA primers pSA-mel-5p: 5'-cac caG GAT CCg acc gtc cgc aag aac-3' (SEQ ID NO: 23) and pSA-mel-3p: 5'-cac AAG CTT tca gac gtc gaa ggt-3' (SEQ ID NO: 24), and inserted into BamHI and HindIII restriction enzyme site in an expression vector pACYC-Duet. And, orf438 genes were PCR-amplified from *Streptomyces antibioticus* genome using two DNA primers pSA-438-5p: 5'-cac CAT ATG ccg gaa ctc acc cgt-3' (SEQ ID NO: 25) and pSA-438-3p: 5'-cac CTC GAG tca gtt ggg ggg gaa-3' (SEQ ID NO: 26), and inserted into NdeI and XhoI restriction enzyme site in the tyrosinase genes-inserted vector to finally construct a tyrosinase expression vector pACYC-Tyr-438.

The mussel adhesive protein fp5h expression vector constructed in Example 1 and the pACYC-Tyr-438 were simultaneously subjected to heat shock at 42° C. for 2 minutes and inserted into *E. coli* BL21(DE3), and a transformant where both vectors are inserted was selected in LB-agar medium containing both ampicillin and chloramphenicol.

The constructed transformant was shake-cultured in common LB medium containing 50 μg/mL ampicillin and 10 μg/mL chloroampicillin at 37° C., and when absorbance ($OD_{600}$) of the culture solution became about 0.8~0.9, inducer IPTG(isopropyl-β-D-thiogalactopyranoside, 1 mM) was added to induce expression of the proteins. After adding IPTG, it was cultured 37° C. for additional 5 hours, and then, the cultured cells were centrifuged at 4000 rpm for 10 minutes, supernatant was removed, and the cells were recovered. The recovered cells were resuspended in a solution for cell disruption (50 mM sodium phosphate buffer, pH 7, 8M urea, 10 mM imidazole), and then disrupted using ultrasonicator.

The tyrosine residue-modified mussel adhesive protein fp5h that was produced by the co-expression was separated and purified from the soluble fraction by nickel column chromatography. Specifically, the protein soluble fraction was subjected to nickel resin-filled column so as to bind protein with the column, and non-bound proteins were washed with washing buffer (50 mM sodium phosphate buffer, 8M urea, 30 mM imidazole, pH 7.0). Proteins were eluted from the column using 0.5 M HCl, and the purified solution was dialyzed using water to remove water and ingredients other than proteins remaining in the protein aqueous solution, and lyophilized to finally prepare purified protein in the form of powder.

7.2. Confirmation of DOPA Residue Content

IRPH assay for specifically detecting DOPA residue was conducted. An IRPH reagent was mixed using a DOPA solution of a known concentration, absorbance was measured at 510 nm to draw a standard curve, and then, an IRPH reagent (0.10 g of o-phenanthroline monohydrate, 0.08 g of ammonium ferric sulfate dodecahydrate, 2 ml of 1M hydrochloric acid, and distilled water added to total 100 ml) was mixed with a test sample and absorbance was measured at 510 nm, and the absorbance was compared to the standard curve, thereby confirming DOPA content in protein, which is shown in the Table 2 below. The result of comparing DOPA residue contents of unmodified fp5h, tyrosinase-treated fp5h manufactured for comparison in the Example, and DOPA-incorporated mussel adhesive protein fp5h according to the present invention was shown below.

TABLE 2

|  | Fp5h (unmodified) | modified fp5h (tyrosinase treated) | DOPA-incorporated fp5h |
| --- | --- | --- | --- |
| IRPH assay | 0 | ~5% | 20-30% |

Since the experiment using an Amino Acid Analyzer of Example 6 hydrolyzes under strong acid condition, among the incorporated DOPA, those modified to DOPA o-quinone or cross linked are hydrolyzed to DOPA again, and thus, total amount of the incorporated DOPA can be analyzed, while since this experiment cannot detect those modified to DOPA o-quinone or cross linked, DOPA content in protein was measured. From the results of Table 2 it can be seen that if DOPA is incorporated according to the method of the present invention, significant DOPA contents may be exhibited compared to tyrosinase co-expression.

---

What is claimed is:

1. A method for producing mussel adhesive protein wherein a tyrosine residue is substituted by DOPA or DOPA o-quinone, comprising the steps of:
   (1) introducing a vector that comprises nucleic acid encoding mussel adhesive protein in tyrosine auxotroph to prepare a transformant;
   (2) culturing the prepared transformant in a tyrosine-free medium to a stationary phase; and
   (3) when the cells reach a stationary phase, adding DOPA (3,4-dihydroxyphenylalanine) or DOPA o-quinone to the medium, and additionally culturing.

2. The method according to claim 1, further comprising the step of (4) separating and purifying the prepared mussel adhesive protein, after the step (3).

3. The method according to claim 1, wherein the tyrosine auxotroph is tyrosine auxotroph of cells selected from the group consisting of Escherichia coli, Pseudomonas, Bacillus, Streptomyces, fungus, yeast, Spodoptera frugiperda (SF9), CHO, COS 1, COS 7, BSC 1, BSC40, and BMT 10.

4. The method according to claim 1, wherein the mussel adhesive protein comprises an amino acid sequence selected from the group consisting of an amino acid sequence as shown in SEQ ID NO: 4, an amino acid sequence as shown in SEQ ID NO: 5, an amino acid sequence as shown in SEQ ID NO: 7, an amino acid sequence as shown in SEQ ID NO: 27, an amino acid sequence as shown in SEQ ID NO: 28, an amino acid sequence as shown in SEQ ID NO: 29, and an amino acid as sequence shown in SEQ ID NO: 6.

5. The method according to claim 1, wherein the mussel adhesive protein comprises at least one selected from the group consisting of an amino acid sequence as shown in SEQ ID NO: 4, an amino acid sequence as shown in SEQ ID NO: 5, an amino acid sequence as shown in SEQ ID NO: 7, an amino acid sequence as shown in SEQ ID NO: 27, an amino acid sequence as shown in SEQ ID NO: 28, an amino acid sequence as shown in SEQ ID NO: 29, and an amino acid sequence as shown in SEQ ID NO: 6 tandemly repeated 1 to 10 times.

6. The method according to claim 1, wherein the mussel adhesive protein comprises an amino acid sequence as shown in SEQ ID NO: 1 or an amino acid sequence as shown in SEQ ID NO: 3.

7. The method according to claim 1, wherein polypeptide consisting of 3 to 25 amino acids comprising RGD(Arg Gly Asp) is attached to a carboxy- and/or amino termini of the mussel adhesive protein.

8. The method according to claim 7, wherein the polypeptide comprising RGD comprises an amino acid sequence selected from the group consisting of amino acid sequences shown in SEQ ID NO: 8 to SEQ ID NO: 17.

9. The method according to claim 7, wherein the mussel adhesive protein comprises an amino acid sequence of SEQ ID NO: 2.

10. A mussel adhesive protein produced by the method according to claim 1, wherein DOPA incorporation rate in total tyrosine is 30% or more.

11. The mussel adhesive protein according to claim 10, further comprising the step of (4) separating and purifying the prepared mussel adhesive protein, after the step (3).

12. The mussel adhesive protein according to claim 10, wherein the tyrosine auxotroph is tyrosine auxotroph of cells selected from the group consisting of *Eschertichia coli, Pseudomonas, Bacillus, Streptomyces*, fungus, yeast, *Spodoptera frugiperda* (SF9), CHO, COS 1, COS 7, BSC 1, BSC40, and BMT 10.

13. The mussel adhesive protein according to claim 10, wherein the mussel adhesive protein comprises an amino acid sequence selected from the group consisting of an amino acid sequence as shown in SEQ ID NO: 4, an amino acid sequence as shown in SEQ ID NO: 5, an amino acid sequence as shown in SEQ ID NO: 7, an amino acid sequence as shown in SEQ ID NO: 27, an amino acid sequence as shown in SEQ ID NO: 28, an amino acid sequence as shown in SEQ ID NO: 29, and an amino acid as sequence shown in SEQ ID NO: 6.

14. The mussel adhesive protein according to claim 10, wherein the mussel adhesive protein comprises at least one selected from the group consisting of an amino acid sequence as shown in SEQ ID NO: 4, an amino acid sequence as shown in SEQ ID NO: 5, an amino acid sequence as shown in SEQ ID NO: 7, an amino acid sequence as shown in SEQ ID NO: 27, an amino acid sequence as shown in SEQ ID NO: 28, an amino acid sequence as shown in SEQ ID NO: 29, and an amino acid sequence as shown in SEQ ID NO: 6 tandemly repeated 1 to 10 times.

15. The mussel adhesive protein according to claim 10, wherein the mussel adhesive protein comprises an amino acid sequence as shown in SEQ ID NO: 1 or an amino acid sequence as shown in SEQ ID NO: 3.

16. The mussel adhesive protein according to claim 10, wherein polypeptide consisting of 3 to 25 amino acids comprising RGD(Arg Gly Asp) is attached to a carboxy- and/or amino termini of the mussel adhesive protein.

17. An adhesive composition comprising the mussel adhesive protein of claim 10 as an active ingredient.

* * * * *